United States Patent
Riley et al.

(10) Patent No.: US 11,883,186 B2
(45) Date of Patent: Jan. 30, 2024

(54) METHODS AND SYSTEMS FOR CONTINUOUS MEASUREMENT OF ANOMALIES FOR DYSMORPHOLOGY ANALYSIS

(71) Applicants: San Diego State University (SDSU) Foundation, San Diego, CA (US); BLUE RESONANCE, LLC, Encinitas, CA (US)

(72) Inventors: Edward Riley, San Diego, CA (US); Ganapathy Chockalingam, Encinitas, CA (US)

(73) Assignees: San Diego State University (SDSU) Foundation, San Diego, CA (US); BLUE RESONANCE, LLC, Encinitas, CA (US)

( * ) Notice: Subject to any disclaimer, the term of this patent is extended or adjusted under 35 U.S.C. 154(b) by 351 days.

(21) Appl. No.: 17/432,925

(22) PCT Filed: Mar. 6, 2020

(86) PCT No.: PCT/US2020/021566
§ 371 (c)(1),
(2) Date: Aug. 21, 2021

(87) PCT Pub. No.: WO2020/181263
PCT Pub. Date: Sep. 10, 2020

(65) Prior Publication Data
US 2022/0183616 A1    Jun. 16, 2022

Related U.S. Application Data

(60) Provisional application No. 62/814,729, filed on Mar. 6, 2019.

(51) Int. Cl.
*A61B 5/00*       (2006.01)
*A61B 5/107*     (2006.01)
(Continued)

(52) U.S. Cl.
CPC ............ *A61B 5/4362* (2013.01); *A61B 5/004* (2013.01); *A61B 5/1079* (2013.01);
(Continued)

(58) Field of Classification Search
None
See application file for complete search history.

(56) References Cited

U.S. PATENT DOCUMENTS

| 6,137,920 A | 10/2000 | Mead |
| 2003/0171566 A1 | 9/2003 | Dean et al. |

(Continued)

FOREIGN PATENT DOCUMENTS

| CN | 108446690 A | * | 8/2018 | ......... G06K 9/00228 |
| CN | 110225761 A | * | 9/2019 | ............. A61K 38/18 |

(Continued)

OTHER PUBLICATIONS

Valentine et al., "Computer-Aided .Recognition of Facial Attributes for Fetal Alcohol Spectrum Disorders" Pediatrics, 2017.

*Primary Examiner* — Mohammed Rachedine
(74) *Attorney, Agent, or Firm* — Greer, Burns & Crain, LTD.; Gregory P. Einhorn; Arik B. Ranson

(57) ABSTRACT

Computer-assisted methods for assisting in anomaly identification relating to a dysmorphology analysis comprise retrieving and/or generating a sequence of progressively changing images that depict morphing of at least a subject's first physical feature, between at least a first state representing an identification of a first anomaly relating to a dysmorphology and a second state representing lack of the identification of the first anomaly. The number of images in the sequence is selected to provide a substantially continuous transition between the first and second states. The retrieved and/or generated images are displayed on a display of a processing device, and a user interface on the processing (Continued)

device is provided for a user to make an image selection, which can then be used to determine identification or lack of identification of the anomaly.

20 Claims, 13 Drawing Sheets

(51) Int. Cl.
| | |
|---|---|
| *G06T 7/00* | (2017.01) |
| *G06V 10/25* | (2022.01) |
| *G06V 40/16* | (2022.01) |
| *G16H 30/20* | (2018.01) |
| *G16H 50/20* | (2018.01) |
| *G16H 50/50* | (2018.01) |
| *G16H 30/40* | (2018.01) |
| *G06T 19/00* | (2011.01) |

(52) U.S. Cl.
CPC .......... *A61B 5/7485* (2013.01); *G06T 7/0012* (2013.01); *G06T 19/006* (2013.01); *G06V 10/25* (2022.01); *G06V 40/165* (2022.01); *G06V 40/171* (2022.01); *G16H 30/20* (2018.01); *G16H 50/20* (2018.01); *G16H 50/50* (2018.01); *G06T 2207/10016* (2013.01); *G06T 2207/10028* (2013.01); *G06T 2207/20081* (2013.01); *G06T 2207/20092* (2013.01); *G06T 2207/30201* (2013.01); *G06V 2201/032* (2022.01); *G06V 2201/07* (2022.01)

(56) References Cited

U.S. PATENT DOCUMENTS

| | | | |
|---|---|---|---|
| 2009/0137544 | A1 | 5/2009 | Li |
| 2013/0158437 | A1* | 6/2013 | Moalem ............... A61B 8/0866 600/587 |
| 2013/0182926 | A1* | 7/2013 | Lee ........................ G06T 5/008 382/131 |
| 2015/0141430 | A1* | 5/2015 | Linask ................. A61K 31/519 514/249 |
| 2018/0195124 | A1 | 7/2018 | Gonzalez et al. |
| 2018/0299430 | A1* | 10/2018 | Kuo ....................... C12N 15/85 |

FOREIGN PATENT DOCUMENTS

| | | | | |
|---|---|---|---|---|
| WO | WO-2017191847 | A1 * | 11/2017 | ............... A61B 5/00 |
| WO | WO-2019064704 | A1 * | 4/2019 | ......... A61B 1/00009 |

* cited by examiner

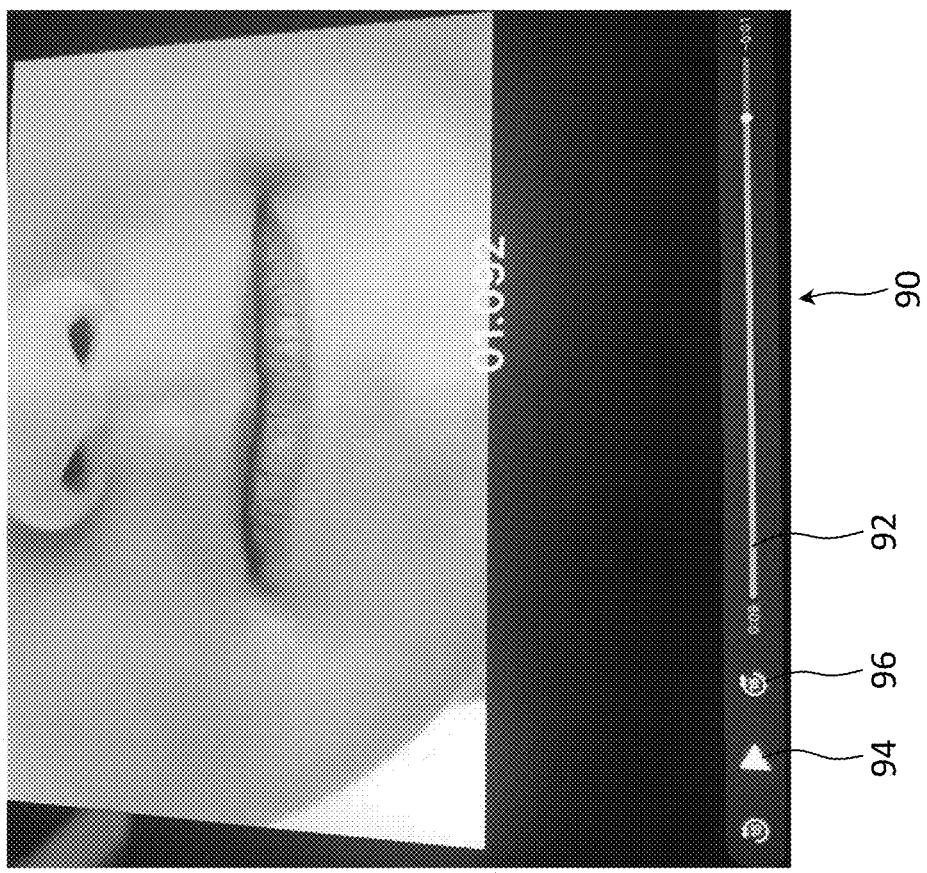
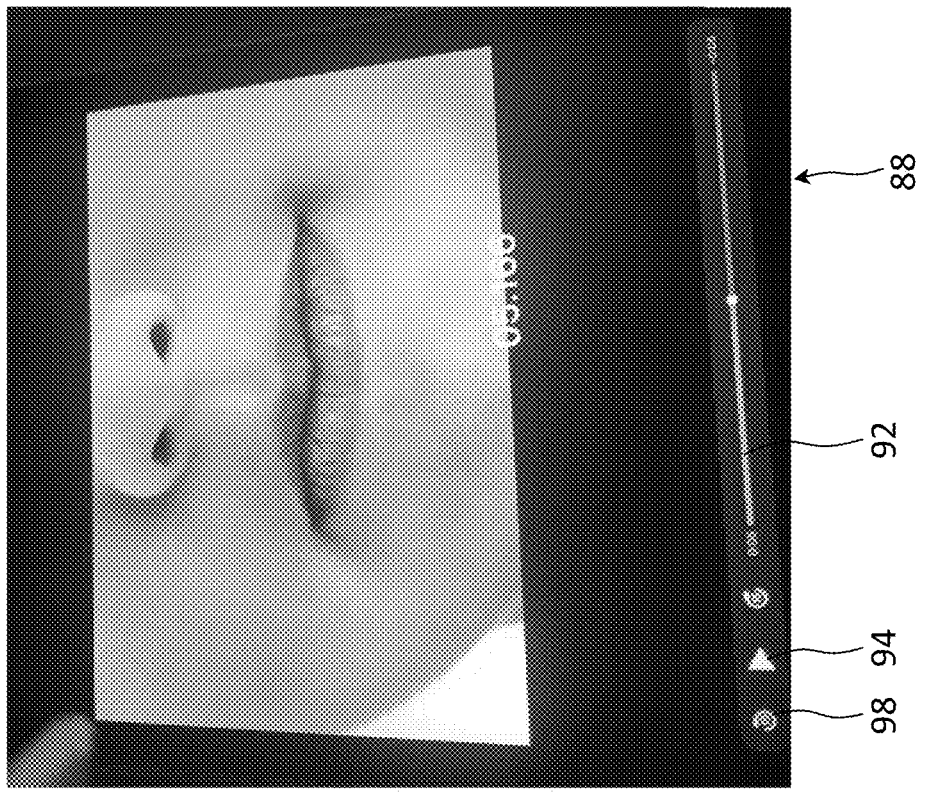
FIG. 6

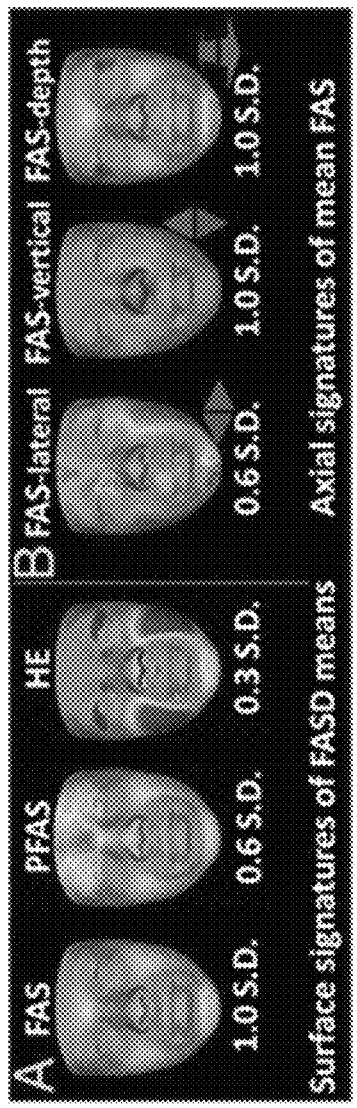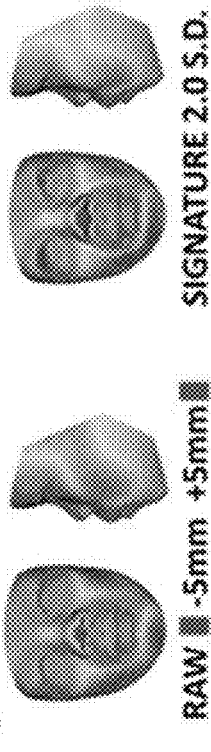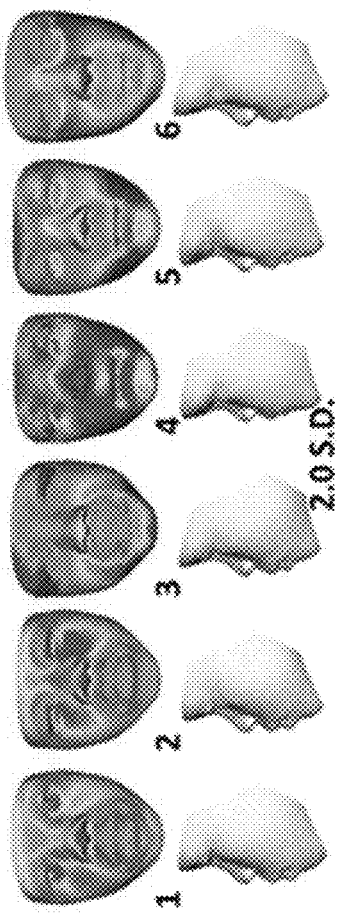
FIG. 10

METHODS AND SYSTEMS FOR CONTINUOUS MEASUREMENT OF ANOMALIES FOR DYSMORPHOLOGY ANALYSIS

CROSS-REFERENCE TO RELATED APPLICATIONS

This national phase application claims benefit of priority under 35 U.S.C. § 371 to Patent Convention Treaty (PCT) International Application PCT/US2020/021566, filed Mar. 6, 2020, now pending, which claims the benefit of priority to U.S. Provisional Application Serial No. (USSN) 62/814,729, filed Mar. 6, 2019, now expired. The aforementioned applications are expressly incorporated herein by reference in their entirety and for all purposes.

FEDERALLY SPONSORED RESEARCH OR DEVELOPMENT

This invention was made with government support under Contract No. 5U24AA014811-15 awarded by National Institutes of Health. The government has certain rights in the invention.

FIELD

The present disclosure relates generally to computer-aided methods and systems for assisting in a dysmorphology analysis for an individual based on identification of one or more anomalies in an individual's physical features. Particular example methods and systems relate to using a mobile communication device (mobile device) to assist in an identification of facial anomalies such as lip thinness and/or philtral smoothness, which is useful for an analysis of fetal alcohol spectrum disorders (FASD).

BACKGROUND

A syndrome is a disease or disorder that has more than one identifying feature or symptom. Each syndrome will have many typical features that are correlated with each other.

For example, teratogenic and genetic syndromes are recognized by distinct changes or alterations in certain facial characteristics (i.e., the facial gestalt). Examples of such changes include changes in the shape of the eye, alterations in the shape and size of the lip, changes in the mid face, alterations in the placement of the ears, and changes in the size and shape of the skull. These changes in facial characteristics may be the first clue that an individual has either been exposed to a teratogen or has a genetic anomaly. Detailed examination of the individual typically precedes genetic testing or in-depth exposure histories.

Such detailed examinations are usually conducted by a specialized healthcare provider or expert, such as a physician, a medical geneticist, a dysmorphologist, etc. who can then identify genetic or teratogenic syndromes. However, determination of this facial gestalt requires a face-to-face examination of the individual by the specialized healthcare provider, since other methods, such as reviewing pictures or videoconferencing, are inherently two dimensional, and not a good medium to make an accurate diagnosis with a high degree of certainty.

Unfortunately, there is a dearth of qualified individuals available to make such assessments. Few such specialists exist even in first world countries, and the demand for their expertise far exceeds the number of people requiring their services. Widespread screening, even in suspected cases, is not easily done. Thus, a proper diagnosis and subsequent treatment of various syndromes remains elusive for the vast majority of the world's population.

For example, a complete analysis of fetal alcohol spectrum disorders (FASD), a consequence of gestational alcohol exposure, is dependent upon the identification of specific facial anomalies, particularly three cardinal facial features—short palpebral fissures, a thin upper vermillion border, and a smooth philtrum. However, as currently measured, there are problems with the assessment of each of these criteria.

For two of these facial anomalies, identification involves the assessment of the thinness of the upper lip (vermillion) border and the smoothness of the two ridges running from the nose to the lip (philtrum), respectively. Currently, these two assessments are performed using a so-called lip-philtrum guide, such as that disclosed in https://depts.washington.edu/fasdpn/htmls/lip-philtrum-guides.htm). The lip-philtrum guide uses five photos assigned to a five-point Likert scale. The Rank 3 picture reflects the population mean (or 50th percentile), while ranks 1 and 5 reflect the extreme ends of the normal curve (<2.5th percentile and >97.5th percentile). Ranks 4 and 5 are consistent with a diagnosis of FAS or partial FAS (pFAS).

However, this Likert scale can be difficult to use, as there is variability on whether someone ranks 3 (NOT FAS) or 4 (FAS) when compared to the photos. For example, it is not clear, for all of the pictures besides the Rank 3, whether the lip pictured in Rank 4 or 5 (those critical for an FAS or pFAS diagnosis) depicts the average of a particular rank or the lower cutoff for that rank. In a Journal of Pediatrics paper by Astley and Clarren (1996), a continuous measure of lip circularity was calculated for each rank, with circularity increasing as the lip became thinner (perimeter2/area). A Rank 4 lip had a circularity of 72.0 (no range or measure of variability was given). In a later paper from the manual of the 4-digit code, a lip Rank 4 picture is shown stating that it has a circularity of 85 (range from 75.5 to 131.4). Hence, the previous Rank 4 would now be a Rank 3, so obviously there is some confusion as to whether a lip is a Rank 4 or not, even by the authors of the guide. In the 1996 paper by the author of the guide, approximately 40% of controls (No FAS, although some may have been alcohol exposed) were assigned a lip Rank of 4 and another 7% had a Rank of 5. In a paper from Australia, the inter-rater reliability for the lip measure, which was done photographically with computerized circularity measures, averaged 0.88, which is strong. However, since it was done with a computerized system using photographs, it means that only 64%-81% of the data are reliable (McHugh, 2012). Finally, in a paper assessing facial characteristics following either marijuana or alcohol exposure, 7% of non-exposed controls had a "definitely thin" lip and 15% had a "somewhat thin" lip.

A similar Likert scale exists for the smoothness of the philtrum, and again there are concerns regarding the images. Initially, only a frontal view of the nose/lip area was used in the rankings, but it became obvious that the depth of the philtral groove was difficult to ascertain correctly from this frontal view alone.

Expert dysmorphologists may be comfortable with assessments using the 5-point Likert scale, given their training and extensive experience with teratogens and genetic defects. However, as other health care providers have been recruited to make a FASD-related anomaly identification, they may not feel comfortable with its limited range. This has created some inconsistencies in which a particular assessment was made. Furthermore, there is a significant mismatch between the number of experts capable of making the anomaly identification and the number of people in need of screening, especially when considering that a large number of affected individuals live in areas without access to such experts.

Both 2D and 3D photographic techniques have also been employed to circumvent some of the issues related to the lip philtrum guide, but these also present problems. The 2D techniques require a high resolution digital camera with zoom and flash and access to a computer with software for analysis. But a majority of diagnoses, particularly those where experts are not available, are made via clinical assessment of features. This is problematic since data suggests that physicians feel unqualified to make these diagnosis for a variety of reasons.

As another example, FAS may be further diagnosed via short palpebral fissures. The palpebral fissure length (PFL) is the distance between the endo and exo-canthion of the eyes. Typically PFL is measured via a plastic ruler by clinicians. However, this can lead to inaccurate results.

There is therefore a need in the art for methods and systems that provide an easier, more convenient, and more consistent assessment of lip thinness and philtrum smoothness for assistance in anomaly identification relating to fetal alcohol spectrum disorders.

There is a further need for simple, reliable, valid, and inexpensive tools by which health care providers can feel more confident in their assessment of an individual, while at the same time maintaining the privacy and confidentiality of the individual.

There is a further need in the art for telemedicine-based methods and systems that allow medical specialists to identify, or assist with identification of, anomalies relating to teratogenic and genetic syndromes, even when such medical specialists are remotely located from individuals (subjects) to be evaluated, and when such medical specialist may not be available at a time when the subject is being evaluated.

SUMMARY

According to one aspect of the disclosed embodiments, provided are computer-assisted methods for assisting in anomaly identification relating to fetal alcohol spectrum disorders (FASD). An example method comprises: retrieving and/or generating a sequence of progressively changing images that depict morphing of at least: a subject's upper lip (vermillion) between at least a first state representing an identification of a first facial anomaly relating to fetal alcohol syndrome (FAS) and a second state representing a lack of the identification of the first facial anomaly; and/or ridges running from the subject's nose to the subject's lip (philtrum) between at least a first state representing an identification of a second facial anomaly relating to fetal alcohol syndrome (FAS) and a second state representing a lack of the identification of the second facial anomaly; wherein the number of images in the sequence is selected to provide a substantially continuous transition between the first and second states; displaying the retrieved and/or generated images as the sequence on a display of a processing device; providing a user interface on the processing device for a user to navigate the displayed sequence and make an image selection; determining a representative image selection based on the user's image selection; processing the representative image selection to determine an identification or lack of identification of the first and/or second facial anomaly; and displaying the determined identification or lack of identification of the first and/or second facial anomaly.

In alternative embodiments, and in combination with any or all of the above, a computer-assisted method is provided for assisting in anomaly identification relating to fetal alcohol spectrum disorders (FASD). The method comprises: retrieving and/or generating a sequence of progressively changing images that depict morphing of at least: a subject's upper lip (vermillion) between at least a first state representing an identification of a first facial anomaly relating to fetal alcohol syndrome (FAS) and a second state representing a lack of the identification of the first facial anomaly; and/or ridges running from the subject's nose to the subject's lip (philtrum) between at least a first state representing an identification of a second facial anomaly relating to fetal alcohol syndrome (FAS) and a second state representing a lack of the identification of the second facial anomaly; wherein the number of images in the sequence is selected to provide a substantially continuous transition between the first and second states; displaying the retrieved and/or generated images as the sequence on a display of a processing device; providing a user interface on the processing device for a user to navigate the displayed sequence and make an image selection; determining a representative image selection based on the user's image selection; transmitting the representative image selection to the additional processing device; and receiving a determined identification or lack of identification of the first and/or second facial anomaly from the additional processing device based on the transmitted representative image; and displaying the determined identification or lack of identification of the first and/or second facial anomaly.

In alternative embodiments, and in combination with any or all of the above, the processing is performed by the processing device.

In alternative embodiments, and in combination with any or all of the above, the processing is performed by an additional processing device, and the method further comprises: transmitting the representative image selection to the additional processing device; and receiving the determined identification or lack of identification from the additional processing device.

In alternative embodiments, and in combination with any or all of the above, generating a sequence of progressively changing images comprises: providing at least one base image; altering the at least one base image to provide, between the altered image and the at least one base image, at least a beginning image and a final image; and generating remaining images in the sequence by progressively altering the at least one base image, beginning image, and/or final image.

In alternative embodiments, and in combination with any or all of the above, said processing the representative image selection comprises: comparing the representative image selection to previously-stored data associating the representative image selection with an identification or lack of identification of the first and/or second facial anomaly; and determining the identification or lack of identification of the first and/or second facial anomaly based on said comparing.

In alternative embodiments, a computer-assisted method for assisting in anomaly identification relating to a dysmorphology analysis comprises: retrieving and/or generating a sequence of progressively changing images that depict morphing of at least: a subject's first physical feature, between at least a first state representing an identification of a first anomaly relating to a dysmorphology and a second state representing lack of the identification of the first anomaly; and/or a subject's second physical feature, between at least a first state representing an identification of a second anomaly relating to the dysmorphology and a second state representing a lack of the identification of the second anomaly; wherein the number of images in the sequence is selected to provide a substantially continuous transition between the first and second states; displaying the retrieved and/or generated images as the sequence on a display of a processing device; providing a user interface on the processing device for a user to navigate the displayed sequence and make an image selection; determine a representative image selection based on the user's image selection; processing the representative image selection to determine an identification or lack of identification of the first and/or second anomaly; and displaying the determined identification or lack of identification of the first and/or second anomaly.

In alternative embodiments, a computer-assisted method for assisting in anomaly identification relating to a dysmorphology analysis comprises: retrieving and/or generating a sequence of progressively changing images that depict morphing of at least: a subject's first physical feature, between at least a first state representing an identification of a first anomaly relating to a dysmorphology and a second state representing lack of the identification of the first anomaly; and/or a subject's second physical feature, between at least a first state representing an identification of a second anomaly relating to the dysmorphology and a second state representing a lack of the identification of the second anomaly; wherein the number of images in the sequence is selected to provide a substantially continuous transition between the first and second states; displaying the retrieved and/or generated images as the sequence on a display of a processing device; providing a user interface on the processing device for a user to navigate the displayed sequence and make an image selection; determining a representative image selection based on the user's image selection; transmitting the representative image selection to the additional processing device; and receiving a determined identification or lack of identification of the first and/or second anomaly from the additional processing device based on the transmitted representative image; and displaying the determined identification or lack of identification of the first and/or second anomaly.

In alternative embodiments, a method for assisting in identification of an anomaly relating to a dysmorphology analysis in an individual comprises: acquiring, by a mobile device, a three-dimensional model (3D model) of a face of the individual using a three-dimensional camera controlled by the mobile device; transmitting, by the mobile device, the acquired three-dimensional model to a remote processor via a communication channel for performing a machine learning algorithm on the acquired 3D model to generate a prediction of the anomaly; and receiving, by the mobile device observational data from at least one VR device. The VR device is configured to receive the generated prediction of the anomaly from the remote processor and display the generated prediction and the 3D model.

An example system comprises a first processing device comprising: a processor; a memory; and executed instructions stored on a non-transitory medium that when executed by the processor cause the processor to perform any of the methods disclosed herein.

An alternative example system for performing any of the above methods comprises: a first processing device comprising: a processor; a memory; and executed instructions stored on a non-transitory medium that when executed by the processor cause the processor to perform any of the methods disclosed herein or any portion thereof; and a second processing device in communication with said first processing device comprising: a processor; a memory; and executed instructions stored on a non-transitory medium that when executed by the processor cause the processor to perform any of the methods disclosed herein or any portion thereof.

According to a complementary aspect, the present disclosure provides a computer program product, comprising code instructions to execute a method according to the previously described aspects; and a computer-readable medium, on which is stored a computer program product comprising code instructions for performing any of the methods disclosed herein.

In alternative embodiments, a system for assisting in identification of an anomaly relating to a dysmorphology analysis in an individual comprises: a mobile device configured to acquire a three-dimensional model (3D model) of a face of the individual using a three-dimensional camera controlled by the mobile device; a remote processor configured to receive the acquired three-dimensional model from the mobile device via a first communication channel and perform a machine learning algorithm on the acquired 3D model to generate a prediction of the anomaly; at least one VR device configured to receive the generated prediction of the anomaly from the remote processor via a second communication channel and display the generated prediction and the 3D model, and to receive observational data from a user of the VR device; and an electronic medical records (EMR) database in communication with the remote processor for exchanging information with the remote processor.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF THE DRAWINGS

The present disclosure will become more fully understood from the detailed description and the accompanying drawings, wherein:

FIG. 6 shows an example sequence of images depicting progressively greater likelihood of a facial anomaly.

FIG. 10 shows example heat maps for anomaly identification for Fetal Alcohol Spectrum Disorder (FASD), according to an example embodiment.

In the drawings, reference numbers may be reused to identify similar and/or identical elements.

DETAILED DESCRIPTION

Introduction

Systems and methods are provided for assisting in dysmorphology analysis. Particular systems and methods will be described for illustration with reference to fetal alcohol spectrum disorders (FASD), in which such analysis is based in part on identification of specific anomalies, e.g., facial anomalies, according to example embodiments of the invention. However, it will be appreciated that example methods and systems are likewise applicable to other dysmorphology analysis.

Example devices, systems, and methods include one or more mobile applications that can be used by, for instance, various health care providers. Such devices, systems, and methods can be particularly useful globally (though this is not required). For example, there is a significant discrepancy between the number of experts (e.g., medical specialists) capable of making an anomaly identification relating to FASD and the number of individuals in need of such services. In the United States, for instance, there are entire states without a single clinical geneticist or dysmorphologist, and in many foreign countries, where FASD is increasingly becoming a major public health issue there may not be a physician for thousands of miles.

Example systems and methods can improve this connection by providing a more portable and accessible way to receive an expert-level anomaly identification in locations where human experts may not be physically present and/or not available when the individual to be evaluated (the subject) is available. Example systems, mobile applications, and methods provide new areas of the application of eHealth or telemedicine technologies in the FASD field or in other dysmorphology fields, and in the assessment of both genetic and teratogen-induced defects.

The term "exemplary" is used herein to mean "serving as an example, instance, or illustration." Any embodiment described herein as "exemplary" is not necessarily to be construed as preferred or advantageous over other embodiments.

Preferred embodiments will now be discussed with respect to the drawings. The drawings include schematic figures that are not to scale, which will be fully understood by skilled artisans with reference to the accompanying description. Features may be exaggerated for purposes of illustration. From the preferred embodiments, artisans will recognize additional features and broader aspects of the invention.

Figure 1:
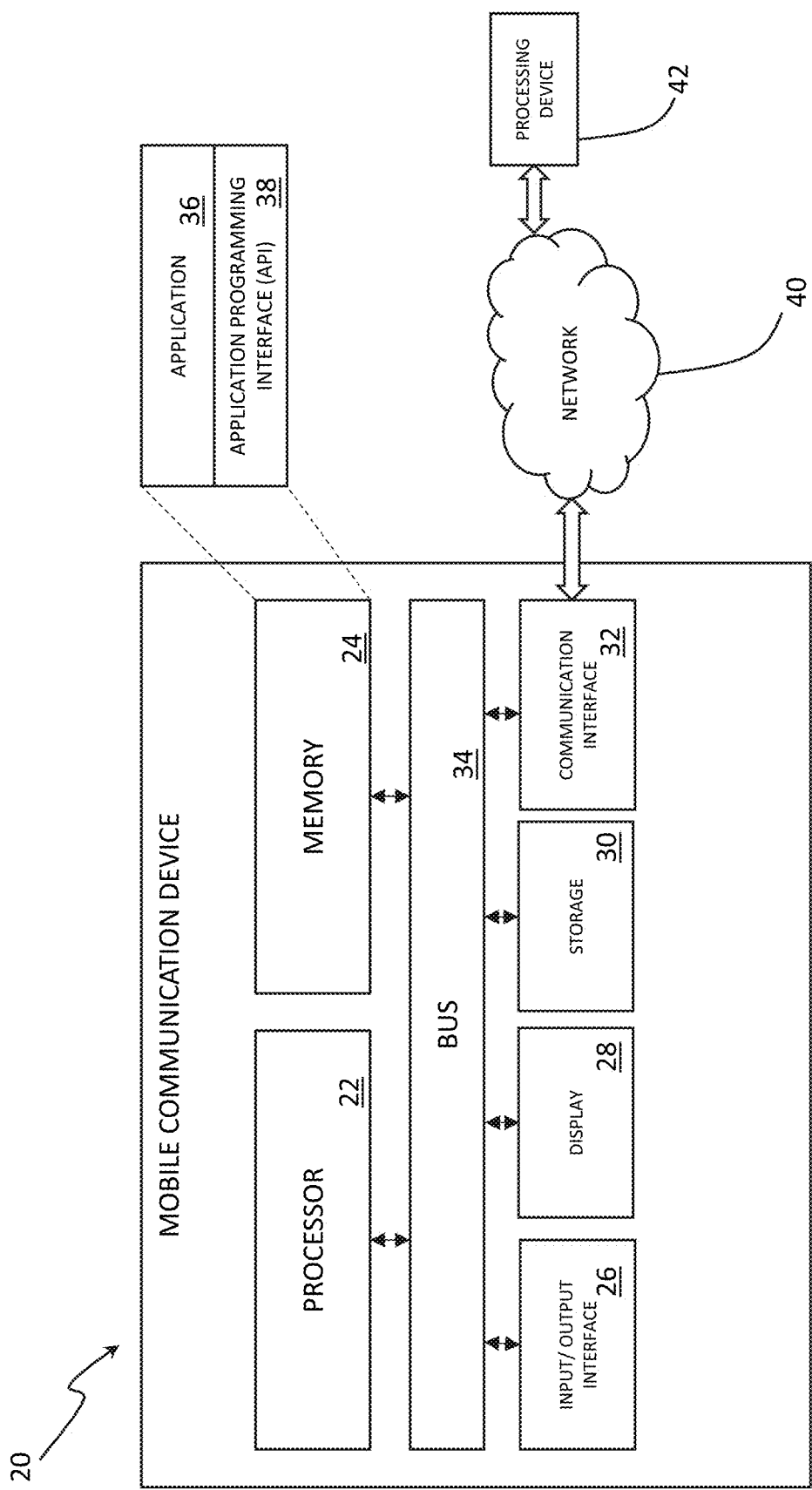
FIG. 1 shows an example system for assisting with anomaly identification relating to a dysmorphology analysis, particularly assessment of fetal alcohol spectrum disorders, according to an example embodiment.

Referring now to FIG. 1, a processing device embodied in a mobile communication device (mobile device) 20 is provided for performing example methods of the invention. However, it will be appreciated that other processing devices such as personal computers, wearable devices, embedded computers, etc. may be used. A particular example mobile device used for illustration is a mobile phone or tablet. The mobile device 20 includes a processor 22, a memory 24, an input/output interface, 26 a display 28, storage 30, and a communication interface 32, which can communicate with one another via a bus 34. An example mobile communication device 20 used herein for executing an example application 36 stored in the memory 24, such as but not limited to a mobile app, is a smartphone, tablet computer, or other so-called "smart" device, such as but not limited to IPHONE™ or IPAD™ by Apple, Inc., GALAXY™ devices by Samsung, or PIXEL™ by Google, Inc., though of course other mobile communication devices can be used.

The memory 24 can include transitory (e.g., random access memory (RAM) and others) and non-transitory memory, and may have stored therein applications 34 including example mobile apps as disclosed herein, along with suitable application programming interfaces (API) 38, middleware, kernels, operating system (OS), etc., as will be appreciated by those of ordinary skill in the art. The mobile app 36 may be stored in a non-transitory memory and/or non-transitory memory or a storage medium (computer-readable medium) for execution by the processor 22. The mobile communication device 20 preferably can communicate with other electronic devices such as other processing devices 40 either over a direct link (not shown), or via a network 42 or cloud, and in some example embodiments can connect with one or more cloud-based devices over the network or cloud. As will be appreciated by those of ordinary skill in the art, the mobile application 36 can preferably be downloaded for installation and/or updates onto the mobile communication device 20 over the Internet, through an application store or "app store," directly through a storage device, pre-installed on the device, or in other ways.

Figure 2:
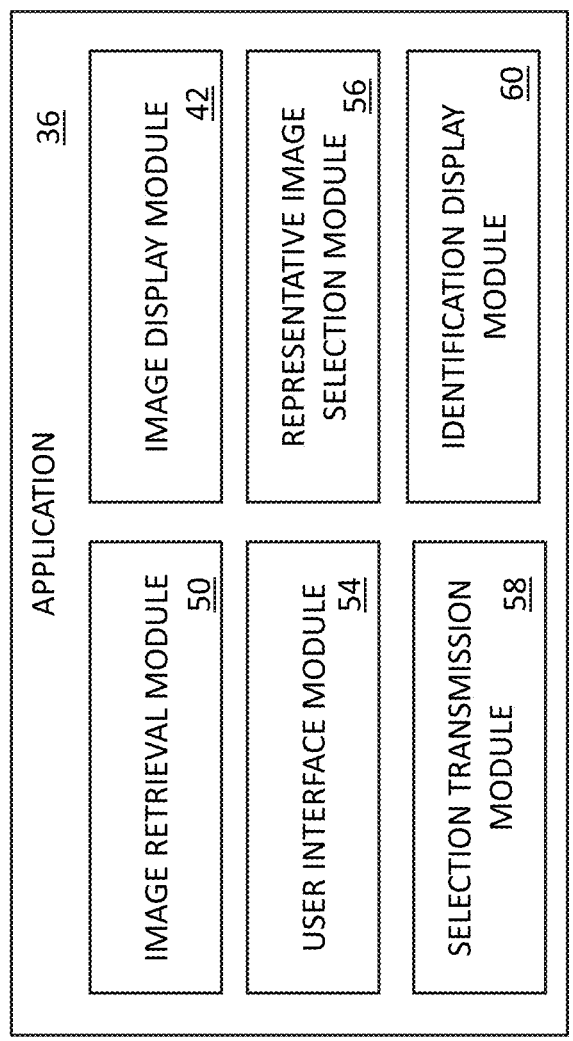
FIG. 2 shows example components of an application (app) executable by a computing device such as a mobile communication device.

FIG. 2 shows components of an example application 36. An image retrieval module 50 is provided for retrieving one or more of a stored sequence of images, which may be generated in advance and stored in a suitable storage on the device 20. An image display module 52 is provided for displaying the retrieved images as a sequence of images on the display. A user interface module 54 is provided for allowing a user to interface with the device 20 to navigate (e.g., scroll through, play back, etc.) the sequence of images and indicate that a particular image or images (preferably, a single image) is selected. A representative image selection module 56 determines the selected image. A selection transmission module 58 optionally transmits the selected image to a separate processing device, such as device 42, for analyzing the selected image. Alternatively, such analyzing may be performed by an analysis module (not shown) in the application 36. An identification display module 60 displays an identification (including identification of a presence, lack of identification, and/or identification of an absence) on the display 28 after receiving from the separate processing device 42 or after analysis via the application 36.

Figure 3:
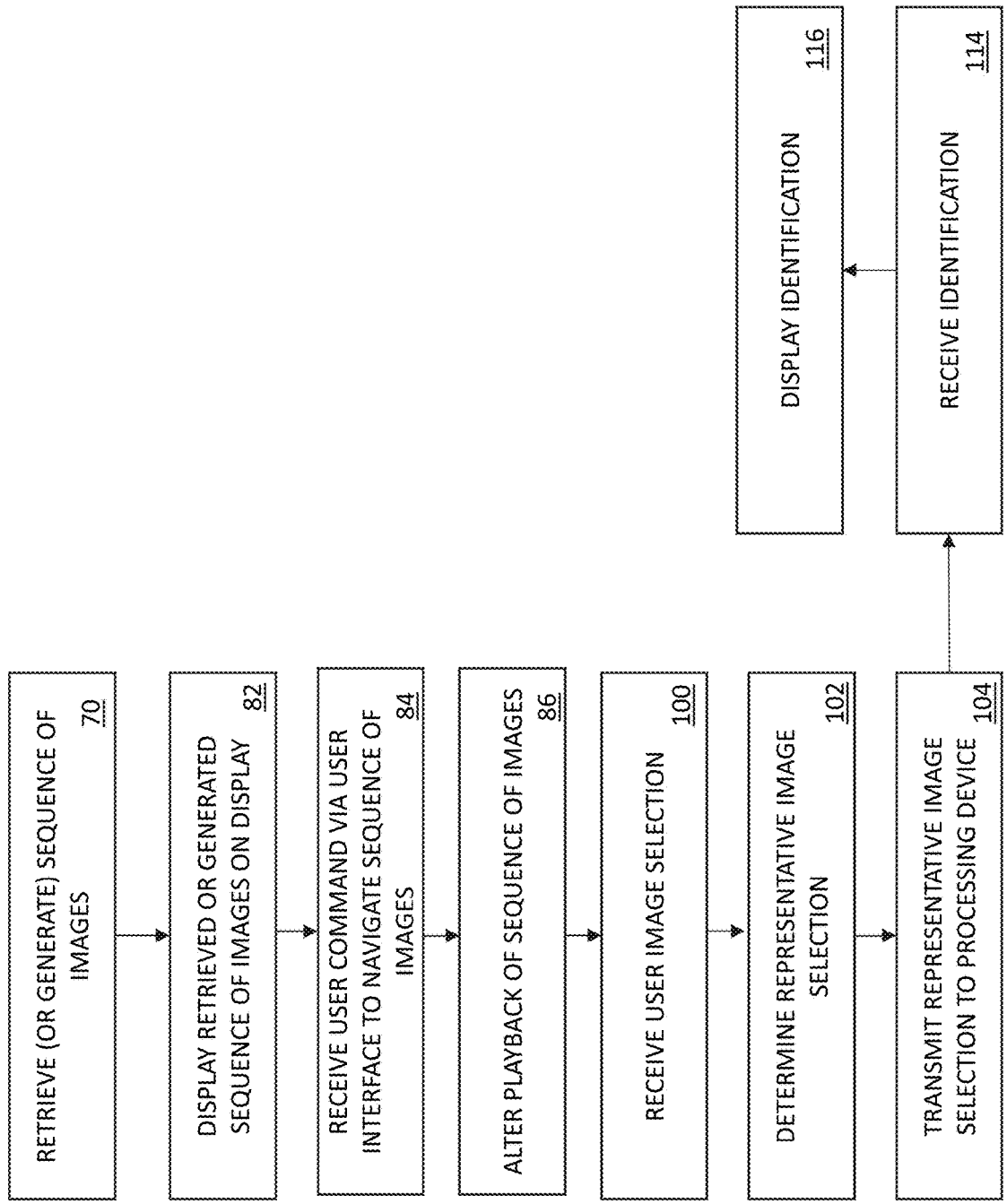
FIG. 3 shows an example method for assisting with anomaly identification performed by the mobile communication device.

FIG. 3 shows an example process for assisting with anomaly identification relating to a particular dysmorphology analysis, including assessment of fetal alcohol spectrum disorders (FASD) that can be performed by a processing device such as but not limited to the mobile communication device 20 having the processor 22 executing instructions from the application 36 stored in memory 24. It will be appreciated that analogous methods to those disclosed by example herein can be applied to other facial features or other physical features to identify anomalies for other dysmorphology analysis.

An example method retrieves, from a storage of preferably previously generated images, or generates as explained in more detail herein, a plurality of images of a portion of a subject's face 70, which in sequence morph the displayed lip (vermillion) (an example of a first physical feature) between at least a first state representing an identification of a first facial anomaly relating to fetal alcohol syndrome (FAS) and a second state representing lack of the identification of the first facial anomaly, e.g., from extremely thin to extremely full. As a nonlimiting example, in the first state, the measurements for the first physical feature may be consistent with a diagnosis of FAS (for example) with respect to that feature, while in the second state, the measurements for the first physical feature may be inconsistent, or not consistent, with a diagnosis of FAS (for example) with respect to that feature (or vice versa). "To" or "between" first and second states as used herein can refer to morphing in either direction, e.g., from first state to or towards second state, or vice versa, from second state to or towards first state. Alternatively or additionally, the images morph ridges running from the subject's nose to the subject's lip (philtrum) (an example of a second physical feature) between at least a first state representing an identification of a second facial anomaly relating to fetal alcohol syndrome (FAS) and a second state representing lack of the identification of the second facial anomaly (again, such morphing can be in either direction).

In an example embodiment, this transition takes place over a large number of steps, and accordingly a large number of images (e.g., 20 steps or greater, 50 steps or greater, 100 steps or greater, 200 steps or greater, etc.) having minor variation (preferably very minor) between consecutive images to provide a relatively seamless morphing animation between the first and second states, e.g., extremely thin and extremely full states for the vermillion.

Figure 4:
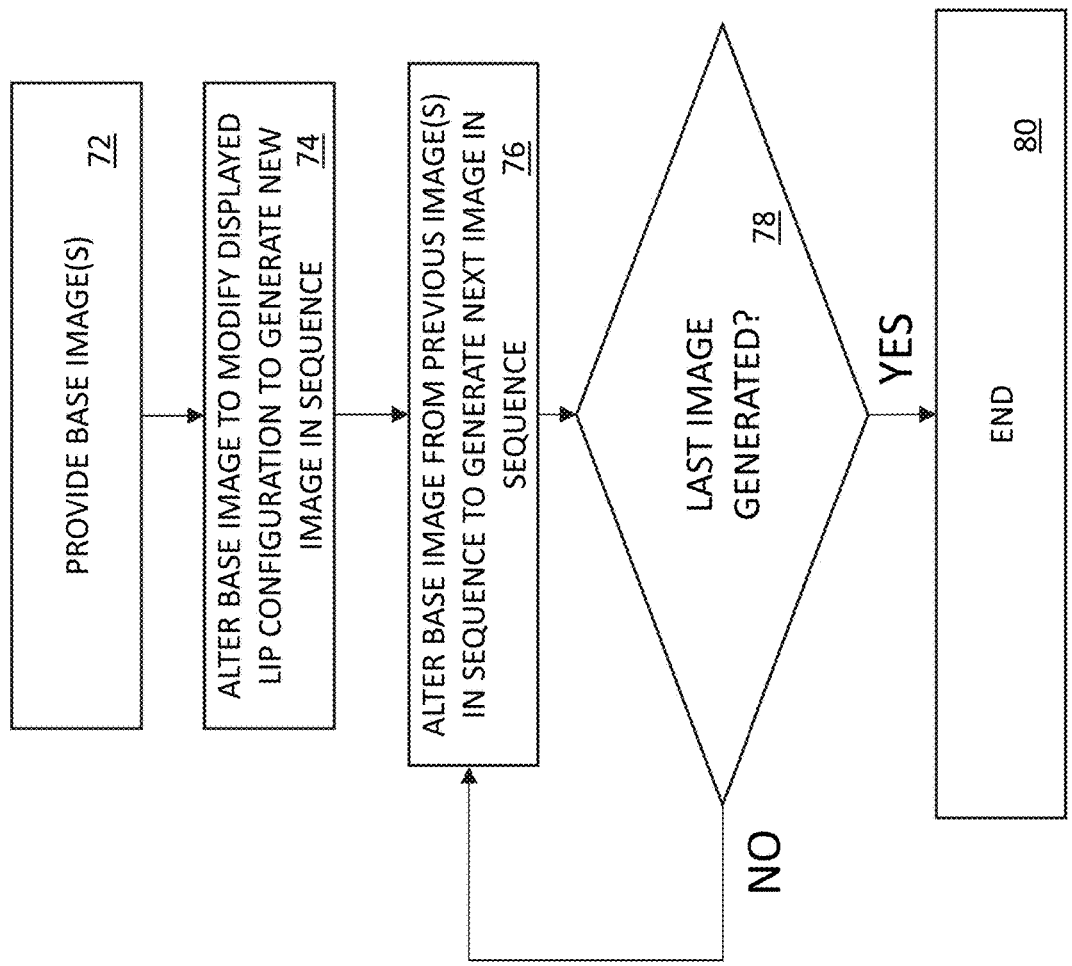
FIG. 4 shows an example method for generating a sequence of images.

FIG. 4 shows an example process for generating images, using lip configuration (vermillion) as an example, though an analogous process can be used alternatively or additionally (e.g., in the same or a separate sequence of images) for the philtrum or for other facial or otherwise physical features. The example process may be performed by a computer or other processor, for instance, executing one or more computer-based image generating and/or editing applications, such as but not limited to ADOBE PHOTOSHOP™ and ADOBE PREMIER™. A nonlimiting example computer is a server that has 16 GB of RAM, Quad Core processor with Intel i5 or i7 series or equivalent with 1 TB hard drive with Windows 10 OS, using. ADOBE™ CREATIVE CLOUD™ suite of tools combined with Java programming language. It is also contemplated to generate such images by the mobile communication device and/or in real time, depending on available processing ability.

To generate images, one or more base images (e.g., photos), such as but not limited to stock photos, generated photos, or otherwise retrieved or generated images depicting a virtual or real subject's face or significant portion thereof is provided 72. Optionally, the provided base image(s) is/are altered to modify a displayed lip configuration, and the altered image is stored as a new image 74. This process can be repeated to generate other new images.

Then, for each remaining image to be generated in the sequence, a previously generated image is gradually altered very slightly between sequential images (e.g., morphed) to progressively modify a displayed lip configuration 76, and the new image is stored. This generates a sequence of progressively changing images showing an extremely thin stage (beginning image) transitioning to progressively fuller stages (intermediate images) and so on to an extremely full stage (final image), with the number of intermediate images affecting the continuity of the transition (greater number=higher continuity/seamlessness and sensitivity, and smaller alteration between images, and vice versa). When a final image in the sequence is generated 78, the process ends 80.

The base images, or images generated from the base image, can be used as intermediate, beginning, and/or final images for generating the example sequence. For example, the base image can be used as an intermediate image, and progressively modified until both the beginning image and final image are generated, or the base image can provide the final image, and be progressively modified until the beginning image is reached. As another possibility, base images can be used for both the beginning and final images, and all intermediate images in the sequence can be generated. As another possibility, base images can be used for one or two among the beginning, intermediate, and final images, an additional one or more images can be generated so that at least a beginning and a final image is provided, and then sequential images can be generated between the beginning and the final image. As another possibility, base images can be used for the beginning, final, and optionally one or more intermediate images, and other intermediate images can be generated to transition from the beginning image through the intermediate images, if any, provided by base images, and to the final image. Other combinations are contemplated as well.

Figure 5:
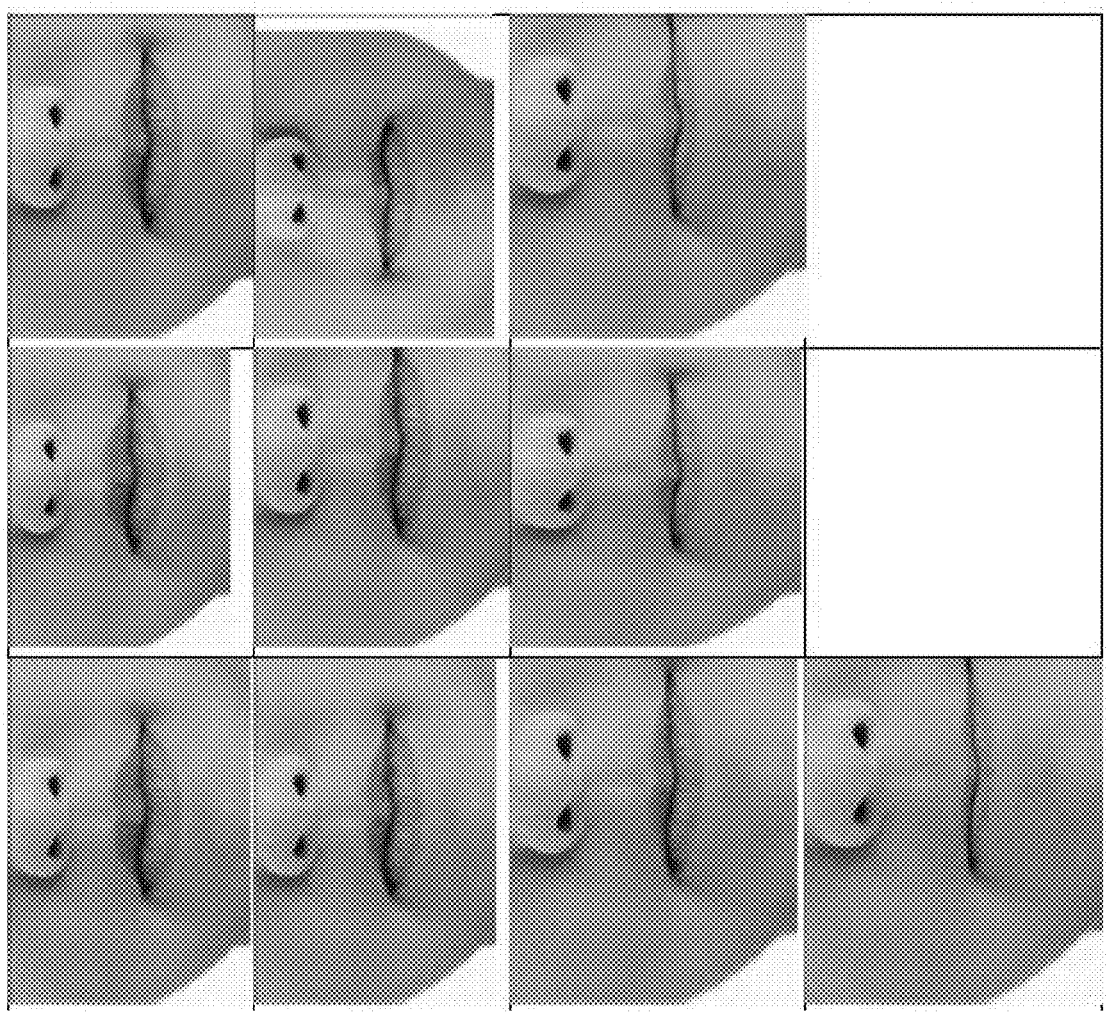
FIG. 5 shows an example method for assisting with anomaly identification relating to fetal alcohol spectrum disorders performed by a computing device, which may be the same computing device as that shown in FIG. 2 or a different computing device.

FIG. 5 shows an example sequence of images. Starting from the upper left image in FIG. 5 and moving from the left to the right image, and then to the next row from left to right, and so on, the thinness of the lips becomes progressively smaller. In morphing these images, across multiple different steps, the images in sequence appear as a movie. Display of this sequence can be controlled by an interactive tool such as but not limited to a slider, in the application 36, providing for a full-scale lip guide unlike the current five point Likert scale, which may be unreliable. Further, rather than using five discrete images the example application 36 morphs between a large number of individual images, making an animation which can be controlled by the user interface. Other image sequences for morphing the philtrum, and/or with both in the same morph, can also be provided.

The thin stage, extremely full stage, and one or more intermediate stages can be derived from or otherwise based on, for instance, analogous lip features in five photos assigned to Likert scale 1-5. However, due to the significantly larger number of generated images, with much smaller respective variation, a much more continuous transition between the images is provided for a similar or equivalent range as provided by the photos assigned to the Likert scale. Greater sensitivity also results.

Referring again to FIG. 3, the generated and stored images (or a subset of generated and stored images, for instance if generation of the complete set of images is limited by network bandwidth, processing or memory resources, storage, etc.) can be displayed 82 in a sequence on a display, such as but not limited to the display 28 of a processing device such as mobile device 20, processing device 42, as part of or in combination with a user interface running on the mobile device or processing device. Preferably, but not necessarily, the processing device is portable, such as (but not limited to) the mobile device 20 executing the mobile application 36. This sequence of images can be displayed so that the movement is animated, analogous to playback of a video.

A hardware and/or software control (or set of controls) provided by the user interface, e.g., provided by the input/output interface 26 and display 28 of the mobile communication device 20, such as a hardware and/or software slider, dial, start/stop, drag/drop, swiping, play/pause/forward/reverse icons, navigation buttons, stick, etc., allows a user to selectively and quickly move between displayed images within the sequence, thus navigating the sequence. Preferably, this control is operable while an image in the sequence is being displayed so that the user can operate the control while viewing the changing image through the sequence. The mobile communication device receives the user command 84, and alters playback of the sequence of images (e.g., starts, stops, moves forward or reverse, etc.) 86 so that the user can navigate to a desired image.

FIG. 6 shows screenshots of an example user interface at two states 88, 90, where each state includes a displayed image in the sequence. A slider 92 on the bottom of the display, along with play/pause 94 and forward and reverse 96, 98 selection icons, provides a user interface for navigating playback and thus cycling or scrolling through the sequence of images.

By using (e.g., interfacing with or manipulating) the control, the user then can select at least one, and preferably one, representative image corresponding to an individual being evaluated, such as by visually comparing the displayed image of the subject's face with the individual's (subject's) face. The mobile communication device 20 receives a selection from the user 100, such as by the user stopping playback on a particular image, clicking on the image, interacting with an icon such as "select," "accept," etc., or in other ways. The selected representative image(s), or other data corresponding to the selected image, such as but not limited to an identifier (e.g., a unique number or code) and/or a state of the control corresponding to that selected image (for instance a slider or dial position, time on a timeline, etc.), provides a selection of a representative image 102 that can be analyzed to determine whether the individual (subject) had features compatible with an FAS diagnosis.

The selection can be analyzed on the same processing device, and/or output, e.g., transmitted, to an external processing device (e.g., processing device 42) 104 by wired or wireless communication, or by storing the selection and transporting a storage device containing the selection as stored data. External devices include but are not limited to a server or cloud device, a connected computer, a (different) mobile communication device, and others.

In a particular example operation of the mobile communication device 20, a user such as a health care provider holds a smartphone next to an individual (subject) being evaluated, such as a patient. The smartphone, through execution of the mobile app 36, displays a beginning image, intermediate image, or final image of a subject's face. The user can then manipulate a control of the mobile app (e.g., slide a slider) to scroll through the sequence of continuous images (either advancing or reversing), and preferably causing the subject's displayed face to animate, until the lip and/or philtrum on the displayed image matches (or substantially matches, or best matches, etc., or is otherwise determined to sufficiently match), that of the individual. This displayed image is then selected, and information relating to the selection is then uploaded via the network 40, e.g., into the cloud, to a server, or to another processing device.

Figure 7:
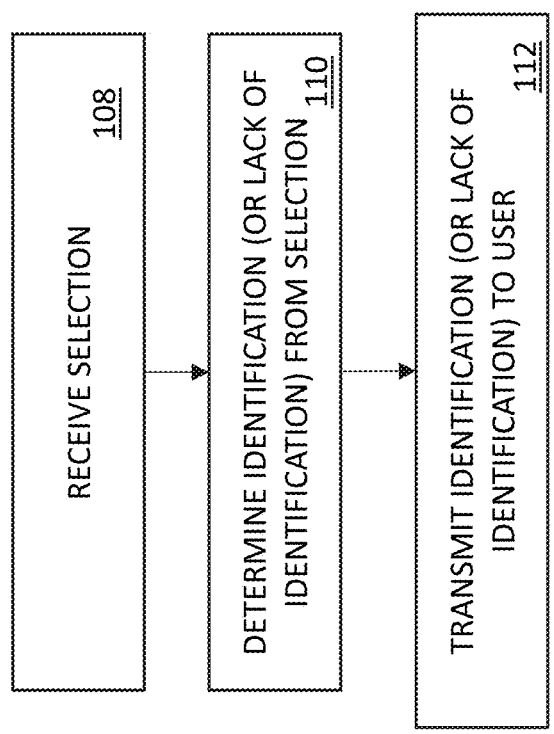
FIG. 7 shows an example user interface presented on a display of a processing device, at stages displaying first and second generated images.

In a particular example method, processing device 42 (see FIG. 1) in or in communication with the mobile device 20 via the network 40, or other processing device, analyzes this selection from the first device (e.g., mobile communication device 20). FIG. 7 shows an example method for analyzing the selection of the representative image. The selection of the representative image, such as via the data provided above, is received 108 by the processing device 42. To determine identification (or lack of identification) 110 in an example method the received selection is compared to a pre-stored table (e.g., a look-up table) or other pre-stored data that associates images in the sequence, or one or more groups of images in the sequence, with an identification or lack of identification of the first and/or second facial anomaly relating to FAS.

As a nonlimiting example, there may be an identification of the first (or second) facial anomaly in a particular image if the measurements for the first (second) facial feature represented by that image or group of images are consistent with a diagnosis of FAS (for example) with respect to that feature, while there may be a lack of identification of the first (or second) facial anomaly if the measurements for the first (second) physical feature represented by the image are inconsistent, or not consistent, with a diagnosis of FAS (for example) with respect to that feature. This association can be, for instance, based on an earlier assessment by experts by evaluation of the sequence of images (such as by operation of the method described above to view the images, or by other methods). Alternatively, the association can be derived from computer-based training, alone or in combination with machine learning. Lack of identification of the anomaly can be provided by, as nonlimiting examples, the absence of positive identification, and/or by a more affirmative result, such as that the specific anomaly was not identified, was determined not to be present, etc.

If, as a nonlimiting example, the initial, intermediate, and final images are generated based on images assigned to a Likert scale, the associated Likert scale images can be used to segment the sequence of images into ranges corresponding to the Likert scale. A determination that the selection falls within one of these ranges can be used to determine that the selection designates an identification or lack of identification of the first and/or second facial anomaly. Similarly, a particular number of an images in a sequence could be used for a threshold (cutoff) over or under which an identification or lack of identification of the first and/or second facial anomaly is determined. It is also contemplated that, for a sequence of continuous images representing multiple anomalies having several, discontinuous ranges (e.g., too thin anomaly identification, medium (lack of anomaly) identification, too wide anomaly identification, etc.), multiple thresholds, threshold ranges, tiers, categories, etc., could be employed. Alternatively or additionally, it is contemplated that the analyzing could be performed in real time by experts interfacing with the processing device 42.

The identification or lack of identification of the first and/or second facial anomaly can then be presented to the user 112, such as by the processing device 42 transmitting the identification or lack of identification of the first and/or second facial anomaly to the first (e.g., mobile communication) device 20, and the first device receiving and displaying the identification or lack of identification of the first and/or second facial anomaly 114 (FIG. 3). The identification or lack of identification of the first and/or second facial anomaly can be displayed 116 on the same display, e.g., the display 28 on the mobile device 20 in which the sequence of images may be displayed, or via a different display. With this example method, the user in real time or in near real time receives feedback on whether the individual had one or more facial anomalies identified that are compatible with part of a FAS assessment (e.g., a diagnosis).

Several problems can be addressed by example methods and systems provided herein. For instance, many pediatricians in the US, despite knowing about FASD, are hesitant to make an anomaly identification and/or diagnosis because they do not feel they have the expertise to accurately identify the features, which can be difficult to measure. Applications 36 performing example methods disclosed herein can provide an easy-to-use tool to make at least one, and preferably at least two, of the measurements nearly automatic and provide a rapid feedback response. This allows them to be more comfortable in making an anomaly identification or a diagnosis based on part on the same, or to at least make a referral to a specialty clinic.

Additionally, there are many places in the US and elsewhere in the world where FASD is a major public health issue, but where there may be little access to physicians or a specialty clinic. For example, the rates among indigenous populations in Canada and Alaska are currently very high, yet access to health care is currently limited, sometimes limited to only visiting nurses. As another example, South Africa (about 10% of children) and Sub-Saharan Africa currently has the highest rates of FAS in the world, but has limited health resources. An example application 36 performing example methods can be portable, and helpful in screening for FASD or other syndromes. Results can also further refer to telemedicine services for further facial imaging diagnosis if needed.

The Likert scale as presently employed is insufficiently sensitive. While the 5-point lip-philtrum guide is supposed to be normally distributed, it has been found that nearly 40% of controls (not alcohol exposed) were labeled as having a thin upper lip. By contrast, example present systems and methods app would make the scale continuous, more sensitive, and more similar to expert dysmorphologist's determinations.

Example methods can be compatible with diagnostic systems recommended by major public health organizations and governments. Example methods can greatly simplify the assessment of lip thinness and philtrum smoothness. They can allow the user to interact with intuitive controls on a portable device to more precisely match the shape and size of the subject's lip region, increasing the specificity of the measurement as compared to using the inflexible 2D photo lip-philtrum guide.

Example applications 36 also allow ethnicity, for instance, to be used as a factor without the need to assess hundreds of people (or more) to determine norms. Only an extreme on each end of the spectrum, for instance, would be needed, and a morph between images can then be made seamless. Providing different base images can thus be used to provide sequences with different photo morphs, for example to take into account differences in ethnicity. Example applications could also be used in the identification of facial anomalies relating to other syndromes with facial dysmorphology.

Example

For further illustration, benefits of example methods will now be explained with respect to fetal alcohol syndrome. Prenatal alcohol exposure can have a devastating impact on the developing fetus, impacting physical and neurological outcomes. Fetal alcohol syndrome (FAS) was initially identified in 1973 by Jones and Smith, and its diagnosis was dependent upon growth retardation, central nervous system abnormalities, and a triad of distinct facial anomalies (short palpebral fissures, a thin upper vermillion, and a smooth philtrum). Shortly thereafter, it became obvious that numerous individuals with histories of heavy prenatal alcohol exposure might be missing one or more of these diagnostic criteria, and the concept of a spectrum of disorders was proposed (Fetal alcohol spectrum disorders—FASD). For example, partial FAS (pFAS) and alcohol related neurodevelopmental disorders were proposed to allow a diagnosis of an individual without all of the facial characteristics or without growth deficiency (pFAS) or an individual with neurodevelopmental disorders (ARND) but without any obvious facial characteristics or growth deficits. FASD is a major public health issue, where accurate early diagnosis might lead to helpful intervention.

However, one reason diagnosis has been hampered is a lack of trained experts. There has been a mismatch in the number of people impacted by prenatal alcohol and current diagnostic capacity, and this disconnect is most apparent in areas where the rates of FASD are the highest or increasing. The number of specialized FASD clinics is limited, and located primarily in North America. Diagnosis is also often hampered by a lack of confidence or knowledge to diagnose FASD by non-specialized physicians or health care providers.

Missed diagnoses or misdiagnosis is common. For example, in a developmental disabilities clinic sample, 86.5% of youth with FASD had never been previously diagnosed or had been misdiagnosed. One possibility to overcome these problems is to utilize health technologies to try and remedy this mismatch between diagnosticians and those impacted.

Current techniques that use photogrammetry, 2D, 3D scans and cloud computing to measure the facial metrics for FAS diagnosis are either very expensive, not portable, inaccurate or a combination of these. A known 2D system works primarily with a diagnostic system, the 4 digit code, which is different than the majority of other diagnostic systems in the world. On the other hand, known 3D systems in use for measurement are expensive and not portable.

Speculation has been made about physicians feeling unqualified to make these diagnosis for a variety of reasons. For example, the lip-philtrum guide is a standard in the diagnostic toolkit for FASD, but it has limitations, such as those explained above, which are believed to contribute to problems in diagnosis.

According to example systems and methods provided herein, such limitations can be avoided by the use of technological features, available at low cost, to assist in the recognition of the cardinal facial features of FAS. Example mobile applications 36 can assist in the recognition of features compatible with a diagnosis of FAS, and such methods and systems can also be applied to the entire spectrum of FASD. Use of mobile technology allows a bridging of the gap between the numbers affected and the number of specialists, while also reducing barriers related to geography. It can further reinforce local clinical judgments with expert knowledge. Example methods can decrease the time for assessment, and remove some of the subjective factors currently plaguing the field.

Limitations of the Likert-scale lip philtrum guide discussed above can be avoided by having a more continuous distribution of both the lip and philtrum, with cutoffs for an identification of facial anomalies determined by expert dysmorphologists working in the field of FAS, and confirmed by comparing against currently available data sets.

In a particular example method, the application 36 morphs a standard picture of the mouth area from a full upper lip to a very thin upper lip as the operator manipulates a slider. When the lip thinness is determined to match (or substantially match, or best match) that of the subject being considered for the diagnosis, the mobile device 20 operator uploads it, e.g., to a cloud based server (an example of the processing device 42), where it is compared to the stored expert's consensus. The mobile device 20 operator can then be notified (e.g., nearly immediately) if the thinness of the lip is a facial anomaly compatible with an FAS diagnosis. Unlike the Likert scale, it is not required to guess whether the picture was between ranks or even if the lip philtrum guide represented an average rank or the lower boundary of that rank. The same approach can be taken with the philtrum using the frontal image from the assessment of the lips and a ¾ image uploaded by the operator.

To illustrate particular example methods, a prototype sequence of images was generated that illustrates the concept of a continuous lip guide. A stock photo of a child who has full lips was obtained and that was set that as the initial state, which is rank 1. The image was then digitally manipulated to achieve a thin upper lip as the final state for rank 5. The task then was to continuously morph the lip from the initial to the final state. ADOBE PREMIER™ Morph Cut was used to achieve a smooth transition. In addition to the initial and final states of the photo, a middle point was also selected that is represents rank 3 of the Lip guide. A smooth animation of the lips was achieved using this example approach.

The animation (sequence of images) was then wrapped using an application to incorporate the user interface (e.g., sliders) and connectivity (e.g., cloud connectivity). The iOS platform from APPLE™ was selected as an example mobile device, and an IPAD™ app was developed using Swift. The example application 36 allows the users to match the lip state in the animation with that of the actual subject via a slider control, such as the control 92 shown in FIG. 6.

To train the processing device 42, experts, e.g., dysmorphologists, were provided with the application 36, and they each were able to mark the cut off points where the identification of a facial anomaly compatible with a diagnosis of FADS occurs. This training can be stored for use by the (e.g., cloud-based) processing device 42 for later diagnosis when receiving a new selection from the mobile communication device 20.

Anomaly Identification Platform Employing a Mobile Device

According to another example embodiment, an end to end system (e.g., a platform) is provided that employs mobile device (e.g., smartphone, tablet computer, etc.) and virtual reality (VR) technology combined with machine learning to make anomaly identification for diagnosis of disorders reliable, scalable, and accessible even in remote areas. A particular example system includes a mobile application (mobile app) executed on a processor of a mobile device that employs a camera to scan a face of an individual to be evaluated (a subject), and generates a high resolution three-dimensional model (3D model) of the individual's face.

The generated 3D model is sent to a remote processor of the example system over a communication channel. "Remote" refers to the remote processor being separately located from the mobile device. The 3D model is analyzed by the remote processor by a machine learning algorithm to generate one or more predictions for assisting with diagnosis and classification of one or more syndromes.

The generated predictions can be delivered, for instance via the communication channel, to the mobile device, e.g., to the mobile application or another application running on the mobile device. The generated predictions, or information derived at least in part from the generated predictions, can be displayed on the mobile device. In some example methods the generated predictions or derived information can be overlaid on a displayed image representing the scan of the individual's face or otherwise displayed concurrently with the scan.

The example system can further include a virtual reality (VR) device, such as a VR headset, separate from the mobile device and in communication with the remote processor. The VR device executes a VR application to display the high-resolution 3D model (or a 3D model derived from the high-resolution 3D model) (a 3D VR model) on the VR device. This 3D VR model may be interactive. The generated predictions, or information derived at least in part from the generated predictions, can be overlaid or otherwise concurrently displayed with the displayed VR 3D model. Additional data, such as data provided and/or derived from electronic medical records (EMR), can also be displayed with the displayed VR 3D model.

The VR device may be used by, for instance, a VR device user such as but not limited to a specialized healthcare provider (e.g., a physician, medical geneticist, dysmorphologist, etc.) who can interact with the displayed 3D VR model. The VR device user can input observational data through the VR application or a separate application, which is then received by the remote processor via the VR application or separate application. This received observational data, or other data derived from the received observational data, can then be provided in whole or in part to the mobile device, for instance for use by the mobile application. Example received observational data resulting from use of the VR device can include, but is not limited to, an identification and/or diagnostic result. Such observational data can also be stored to provide new or updated EMR data.

In this way, a mobile device located with an individual to be assessed can be used to generate a 3D model. The 3D model can then be remotely analyzed automatically by the remote processor executing one or more machine learning algorithms and/or manually by a VR device user (e.g., a specialized healthcare provider). The results of both the automatic and manual analysis can be based in part on EMR data that can be provided to the remote processor and/or to the VR device, and can generate additional (e.g., new or updated) EMR data that can be provided to the mobile device and/or to an EMR database.

Figure 8:
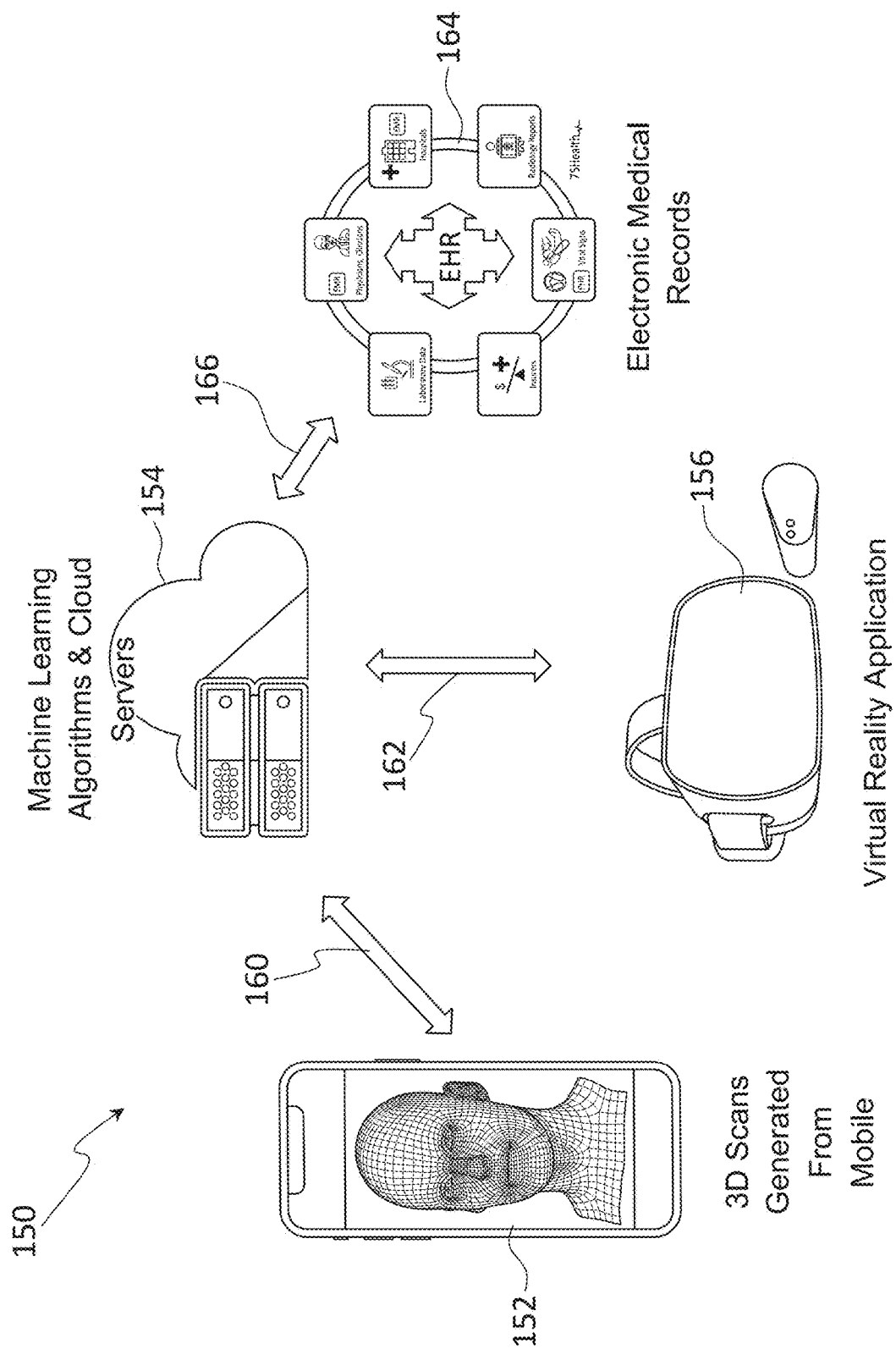
FIG. 8 shows an example system architecture for assisting with anomaly identification, according to another embodiment.

FIG. 8 shows an example system or platform architecture 150 for performing example methods. The system 150 includes a mobile device 152, a remote processor 154, and one or more virtual reality devices (VR devices) 156. Reference to a single VR device 156 is intended to likewise refer to multiple VR devices where multiple VR devices can be employed. The mobile device 152 communicates with the remote processor 154, such as but not limited to a cloud based server, over a first communication channel 160. The first communication channel 160 can be wired or wireless, or a combination. Additionally, the remote processor 154 communicates with the VR device 156 over a second communication channel 162, which can be wired or wireless, or a combination. The remote processor 154 and the VR device 156 may be similarly located (e.g., a server located at the same premises as the VR device), located remotely from one another (e.g., a cloud based server in communication with both the mobile device 152 and the VR device), or a combination (e.g., a subset of the VR devices located at the same premises as a server, with others of the VR devices located at a remote premises). The remote processor 154, and (at least indirectly), the mobile device 152 and/or VR device 156 can be in communication with one or more databases 164 storing electronic medical records (referred to herein as EMR databases) over a third communication channel 166, which communicaton channel may be wired or wireless, or a combination. The EMR databases 164 may be co-located with the remote processor 154 or located remotely. The first, second, and/or third communication channels 160, 162, 166 can be provided in some example embodiments by one or more networks including local area networks (LANs), wide area networks (WAN), cellular, satellite, or other mobile networks, internet, or any combination of these or others.

The example mobile device 152 can be configured similarly to the mobile device 22 in FIG. 1 or otherwise configured, and can be embodied, for instance, in a smartphone (or other so-called smart device, such as a tablet computer, etc.) having a processor, a memory storing executable instructions for running a mobile application to perform one or more methods described herein. The mobile device 152 also includes a three-dimensional (3D) camera. "3D camera" is intended to refer to any device, including but not limited to a camera, capable of producing three-dimensional images (which can be represented by image data) of an object in a field of view of the device. The 3D camera can be integrated into the mobile device 152, a nonlimiting example of which being a true depth camera. In other embodiments, the 3D camera can be coupled to the mobile device 152, e.g., as an external accessory, and reference herein to a mobile device "including" a 3D camera is intended to likewise refer to a mobile device having an integrated 3D camera as well as a mobile device operating a 3D camera coupled to and controlled by the mobile device.

Figure 9:
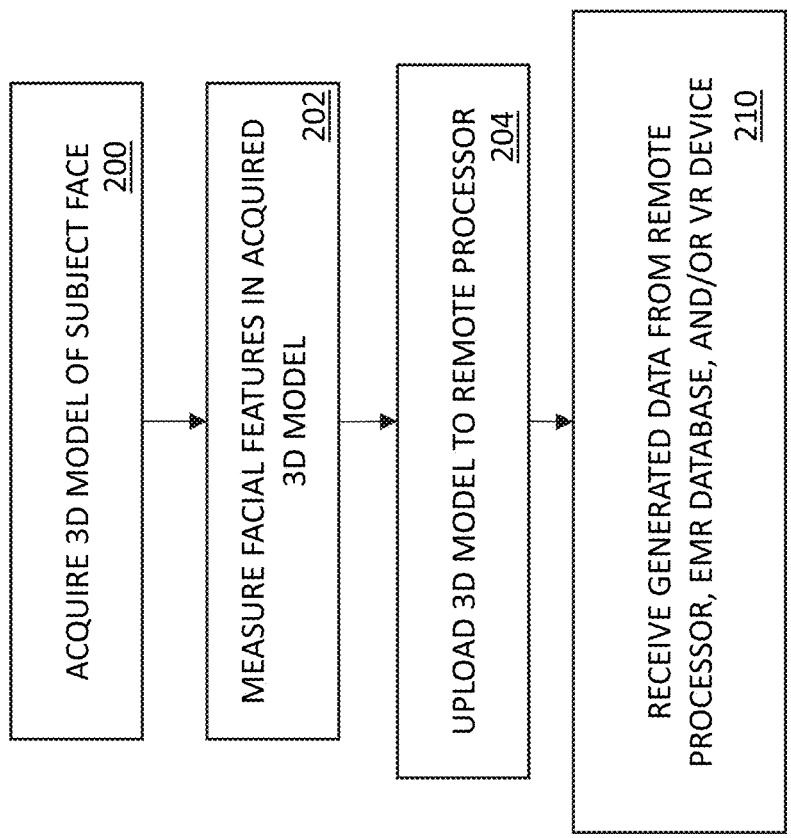
FIG. 9 shows an example method performed by a mobile device in the system of FIG. 8.

FIG. 9 illustrates an example method performed by the mobile application executed on the mobile device 152. The mobile application can be configured to operate the 3D camera when executed to scan and generate (e.g., acquire) a high resolution 3D model of an individual 200. For example, the mobile application can receive a command from a user of the mobile device 152 to operate the 3D camera using known methods, and begin a scanning (image acquiring) and image processing operation to produce the high resolution 3D model. "High resolution" refers to the 3D model having a sufficient resolution such that a human user, the remote processor, or both can distinguish one or more selected facial gestalt features or portions of such features within the image to perform processing in example methods. Example resolutions for the 3D model may be on the order of centimeters, millimeters, sub-millimeters, etc.

Complex and expensive camera infrastructures conventionally have been used to generate 3D models. However, many recent smartphones and tablet computers, such as but not limited to recent models of IPHONE™ and IPAD™ manufactured by Apple, Inc., and other mobile devices, include true depth cameras that use so-called "structured light" technology. Smartphones and tablet computers may use this technology to produce a 3D model of a face (e.g., a user's face) for identification purposes, for example.

The example mobile application utilizes such true depth cameras and structured light technology to acquire 200 (e.g., capture using the 3D camera and generate) a highly detailed 3D model of an individual's face. Preferably, this acquisition 200 is performed relatively quickly (e.g., on the order of seconds, and in a particular example 15 seconds or fewer). The example mobile application uses one or more mobile device application programming interfaces (APIs) (e.g., smartphone APIs exposed by a smartphone manufacturer) that allow developers to leverage the capabilities of the true depth cameras in the mobile devices to generate a 3D model of the face with 300,000 3D face points. An example 3D model can be generated in 15 seconds or fewer.

In some example embodiments, the mobile application can also be configured to measure one or more facial features in the generated 3D model 202. Examples of such facial features that may be measured by the mobile application include, but are not limited to, palpebral fissure length, eye width, lip curvature, lip outlines, or philtral smoothness. Alternatively, one or more of these measurements can be performed by the remote processor 164.

The mobile application then uploads 204 the high resolution 3D model, or 3D model derived from the high resolution model (e.g., after upscaling or downscaling, compressing, filtering, etc.) (collectively, the 3D model) to the remote processor 154 over the first communication channel 160. An example remote processor 154 is a cloud based server, although other servers or processors can be provided. It will be appreciated that a server as used herein can refer to one or more servers, and reference to a "server" is intended to be likewise applicable to multiple servers. The remote processor 154 can also be in communication with the EMR database 164 over the third communication channel 166. An example cloud based server or other remote processor can be configured to include suitable security (e.g., Health Insurance Portability and Accountability Act (HIPAA) compliant servers) for receiving, storing, and/or processing medical information, as will be appreciated by an artisan.

Figure 11:
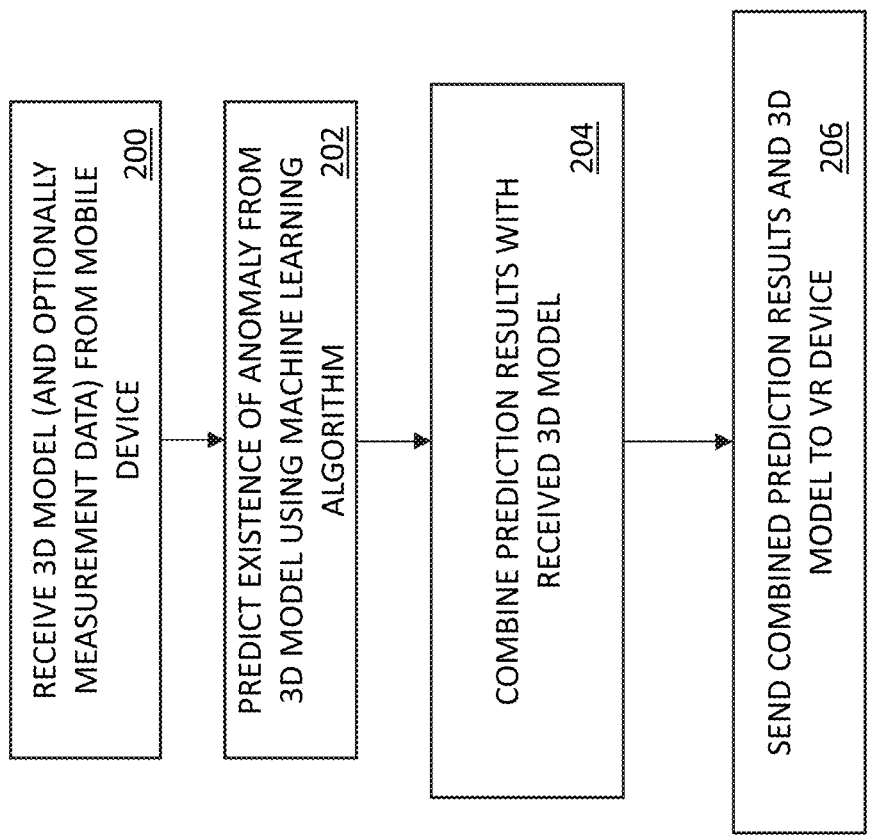
FIG. 11 shows a prediction method for identification of anomalies performed by a remote processor using a generated 3D model, according to an example embodiment.

FIG. 11 shows an example method performed by the remote processor 154. The remote processor 154, e.g., cloud based server, receives the 3D model 210, and optionally measurement data if generated, from the mobile device 152 over the first communication channel 160. Additionally, the remote processor 154 may receive and employ data from the EMR database 164 in communication with the remote processor as additional data for use by the remote processor where available, although this is not required in all embodiments.

The remote processor 154 then executes 202 one or more machine learning algorithms using the received 3D model as input (and optionally, additionally from the data received from the EMR database 164) to make predictions related to the existence of one or more syndromes. For example, the cloud based server may use the machine learning algorithms to assess several facial characteristics and generate one or more predictions of the existence of one or more anomalies in the subject's face based on the assessed characteristics. An example machine learning algorithm executed by the remote processor 154 is a supervised learning classification algorithm such as support vector machines, random forest, and/or neural networks.

A particular example prediction method performed by an example machine learning algorithm will be described with reference to identification of anomalies relating to Fetal Alcohol Spectrum Disorder (FASD). It will be appreciated that identification of anomalies relating to other syndromes can be predicted using similar methods.

The received 3D model from the remote device 152 may be initially processed (e.g., using image processing methods such as decompressing, filtering, scaling, anti-aliasing, smoothing, rotating, etc.), though this may not be required. RAW images may be used in some example embodiments. The remote processor 154 generates one or more heat maps from the 3D model. Example heat maps are shown in FIG. 10. A machine learning algorithm then compares the generated heat maps from the 3D model to one or more stored surface signatures associated with FASD means (e.g., FAS, partial FAS (pFAS), and/or nonsyndromal heavily exposed (HE)) and/or axial signatures of mean FAS (e.g., FAS-lateral, FAS-vertical, FAS-depth).

Based on this comparison with the surface signatures, the machine learning algorithm outputs prediction results. Prediction results can include, for instance, a prediction as to the likelihood that the generated heat map corresponds to one or more anomalies corresponding to the stored FASD (pFAS, HE, etc.) means. This output can be represented by, for instance, percentiles of facial features or other proportions, predicted classification results, and/or proposed alcohol exposure. One or more prediction vectors and/or one or more predicted classifications, can be generated by the machine learning algorithm representing the predictions.

For example, FIG. 10 shows at (A) example surface signatures of FASD means (FAS—1.0 SD; PFAS—0.6 SD; HE—0.3 SD) and at (B) axial signatures of mean FAS (FAS-lateral—0.6 SD; FAS-vertical—1.0 SD; FAS-depth—1.0 SD). At (C), a surface comparison is made of a heat map of an individual with FAS (RAW), e.g., a heat map from a received 3D model, to a signature 2.0 SD. At (D), signatures and profiles of six individuals in HE category (2.0 SD) are shown.

An example method trains the example machine learning algorithm (e.g., a neural network or other model) by inputting training data including (e.g., vectorized) heat maps from individuals that have been previously associated (or not associated) by experts with one or more anomalies (or stages, degrees, signatures, etc.) corresponding to one or more syndromes to be assessed. The machine learning algorithm generates predictions and/or classifications of such anomalies (stages, degrees, signatures, etc.) from the received heat maps. These predicted results are compared to the expert data (e.g., ground truth data), and the machine learning algorithm (model) is updated accordingly, using training methods that will be apparent to those of ordinary skill in the art. The trained algorithm (e.g., the trained model) can then be used in inference to evaluate the generated heat maps from the received 3D models.

The prediction results generated from the machine learning algorithm can optionally be stored on the remote processor 154, provided to the mobile device 152, e.g., via the first communication channel 160, and/or provided as EMR data (or data that is processed to provide EMR data) to the EMR database 164 via the third communication channel 166 to be entered (e.g., stored) in the EMR database. Additionally, in an example embodiment, the prediction results are combined 204 with (e.g., overlaid with, displayed with, enhanced using, etc.) the 3D model generated by the mobile device or a version derived therefrom, and then provided to the VR device 206 via the second communication channel 162. In example embodiments, the remote processor 154 can combine the 3D model and prediction data by, for instance, overlaying a prediction, a classification, one or more prediction or classification scores, charts, graphs, or other indicators representing any of the above, etc. on the 3D model to be displayed, then sending the overlaid or enhanced 3D model to the VR device. The remote processor 154, for instance, can also send other generated data, such as any processed 3D model, the heat map, etc. and/or the resulting prediction data to the VR device 156 and/or to the EMR database 164. The VR device (or a subset of multiple VR devices) may be located in the vicinity of the cloud based server, or may be located remotely from the cloud based server.

On the VR device 156, the combined prediction and 3D model data is received from the remote processor 154, and displayed on the VR device for viewing by a VR device user. Example VR device users include, but are not limited to, experts including medical specialists, and in a particular example dysmorphologists. The received data can be viewed using a VR application stored in memory and executed by a processor on the VR device for generating VR displays and interacting with VR users using methods provided herein. Any suitable virtual reality device or combination of devices may be used for the VR device 156. Nonlimiting example VR devices include Oculus Rift, Oculus Go, Oculus Quest, HTC Vive, Gear VR, etc. In some example VR applications, the displayed VR 3D models may be able to be manipulated and be viewable in any angle using the executed VR application.

An example 3D model viewed by the VR device (VR 3D model) using the example VR application can, but need not in all embodiments, further include information provided by the EMR databases (or other EMR source) such as, but not limited to, x-ray films or images, laboratory results, scans, drug history, etc. The combined 3D model and prediction data with associated overlays and/or enhancements can provide a virtual scene to be viewed by the VR device 156. In example embodiments, objects in such virtual scenes can be manipulated within the VR application, e.g., using any suitable interface such as but not limited to a controller, head or eye tracking, or any other interface.

The VR application may also allow VR users to record their observations through the VR app (though other applications may be used for this) to provide observational data, which can in turn provide updated EMR data. Such observational data can also be displayed with the VR 3D models. For instance, multiple VR devices can be employed in one or more locations, each receiving the data from the remote processor 154 at one or more time instances, so that multiple VR users located in diverse locations can view and share each other's findings. A virtual scene can further include, for instance, diagnoses from other VR users (experts) having access to the same data or other data.

Further, in some example embodiments, VR users can interact with the displayed VR 3D model using suitable interfaces (e.g., controllers) to provide additional observational data. For instance, a VR user can indicate (e.g., mark) points on the displayed face using a controller and compute the distance between the points to provide facial measurements. Such measurements can be received by the VR app (or other app operating with the VR app), stored, provided to the remote processor 154 and/or the EMR database 164, or otherwise processed. An example of this processing includes comparing the input facial measurements to database norms available for 3D facial measurements. In example embodiments, VR users can enter observations such as but not limited to diagnoses and/or notes via the VR app (or other app operating with the VR app), which observations can be stored, provided to the remote processor and/or the EMR database, or processed. Observations can also be used as additional training data for further training of the machine learning algorithm.

Referring again to FIG. 9, generated data such as but not limited to the prediction data or other data generated by the remote processor 154, medical data provided from the EMR database 164, and/or observational data input via the VR device 156, in any combination, can be sent to the mobile device 152, e.g., via the remote processor 154. This data is then received 210 by the mobile device 152. Receipt of such data 210 can be in real time or at a selected future time. By providing such generated data to the mobile device 152, a user of the mobile device, e.g., remotely located with respect to the remote processor 154 and the VR device 156, can receive useful information relating to the assessment of one or more anomalies in the subject for which the mobile device has captured a 3D model.

Example methods and systems can significantly improve telemedicine in situations where the image available to the healthcare provider is available in 3D, even via a remotely located mobile device. Example systems and methods thus are scalable and provide accessibility even in remote (e.g., rural) areas. Additionally, the generated 3D images and/or the displayed 3D VR images in some example embodiments can be made available to users (e.g., healthcare provider) off-line to be viewed anywhere in the world and at any time. Such example systems can thus provide asynchronous medical consultation, without the need for the medical specialist and the individual (subject) being assessed to be online at the same time, as in conventional telemedicine methods. Further, as example mobile device applications can be implemented in existing mobile devices capable of producing images for example 3D models, costs of example systems can be minimized.

Figure 13:
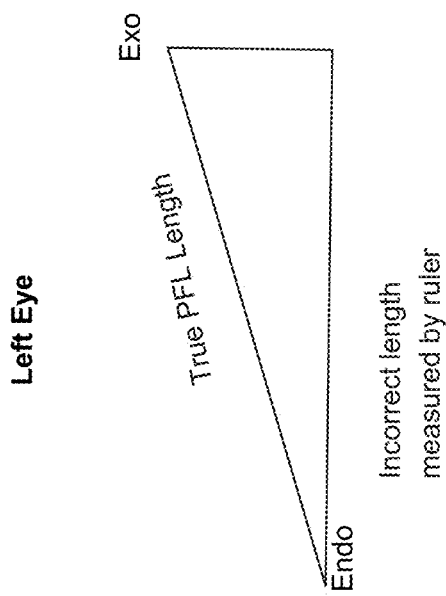
FIG. 13 illustrates a comparison between a conventional method for PFL measurement and a PFL measurement generated using example methods.

Nonlimiting example methods will now be discussed with respect to identifying anomalies related to fetal alcohol syndrome. As explained above, palpebral fissure length (PFL) is the distance between the endo and exo-canthion of the eyes. Typically, PFL is measured via a plastic ruler by clinicians. However, such measurement can lead to inaccurate results for several reasons. One reason is that it is difficult to reach the endo and exo-canthion with a measuring instrument such as a ruler or a caliper due to its location and the curvature of the eyes. Another reason is that the distance measured is the planar distance, which is based on an incorrect assumption that the endo and exo-canthion are in the same vertical plane. Instead, the exo-canthion is typically seated deeper in the face than the endo-canthion. FIG. 13 illustrates errors that can be generated by using such typical methods. While software tools exist that can measure PFL using two-dimensional photographs after manually landmarking the exo and endo-canthion, these tools generally exhibit similar drawbacks.

Example methods disclosed herein can generate a 3D image (scan) of an individual's face using the mobile device application to provide the 3D model. The mobile device 152 executing the mobile application (or, alternatively, the remote processor 154) can quickly (e.g., 20 seconds, but can be greater or fewer) automatically process this generated 3D model to, for instance, landmark the endo and exo-canthion and compute the distance between them as a distance measurement. The landmarking of the facial features are achieved using, for instance, a library (as a nonlimiting example, iOS Scenekit library) that may be provided as part of the mobile device 152 operating system or otherwise available.

Figure 12:
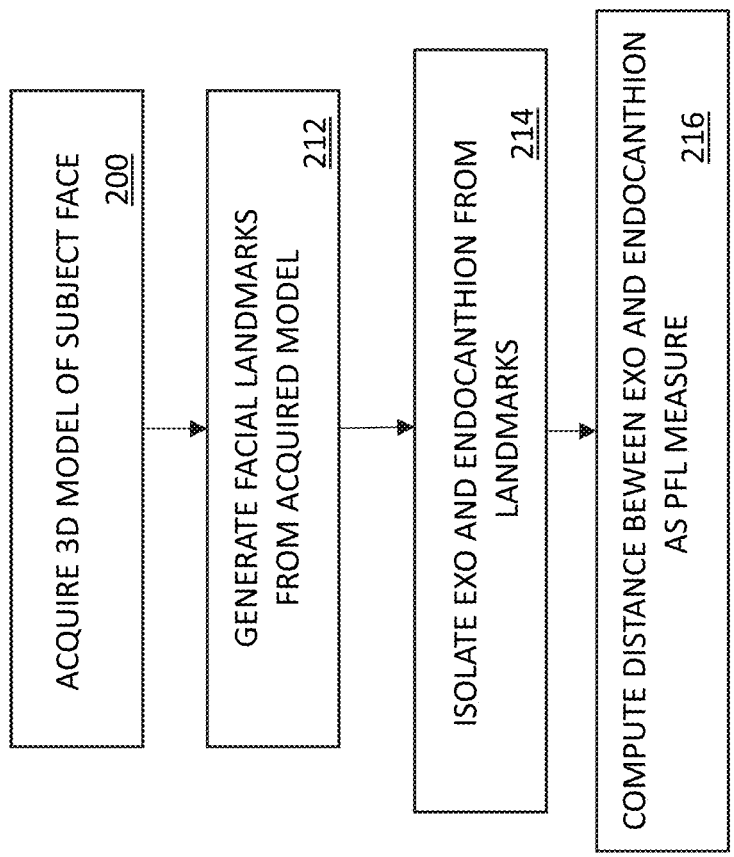
FIG. 12 shows an example method for automatically measuring PFL from a 3D model, according to an example embodiment.

An example method for automatically measuring PFL is illustrated in FIG. 12. The example method can be implemented using a library such as but not limited to iOS Scenekit. The 3D model of the subject's face is acquired 200, such as by using the mobile device 152 as explained herein. Facial landmarks are generated from the acquired 3D model 212. The exo and endocanthion are then isolated from the landmarks 214, and a distance between the isolated exo and endocanthion landmarks is computed to provide the PFL measure 216.

This measurement method provided in FIG. 12 can provide a true PFL length, as further illustrated in FIG. 13, as it uses a 3D model of the face. Accuracy of example methods can be, for instance, on the order of 0.1 mm. Furthermore, example mobile apps can allow for a user to manually input location data, for instance to manually locate the endo and exo-canthion, to supplement or replace the automatically generated locations if it is believed that these points were not accurately landmarked. The example mobile app can then compute a new distance measurement based on the updated landmarks.

Example facial characteristics can thus easily be measured using example methods as provided herein, which can assist a local healthcare provider with a diagnosis even though an expert in such minor facial anomalies might be located thousands of miles distant. Example techniques may be useful in assisting with the diagnosis of genetic syndromes with characteristic facial features where genetic testing is not available or the cost is prohibitive.

By further providing machine learning capabilities via the remote processor 154 using the 3D image, the remote processor itself can make an initial diagnosis or screen for particular defects. Training data for machine learning algorithms for some dysmorphic syndromes can be provided by, as a nonlimiting example, two dimensional photographs outlining a number of dysmorphic syndromes in various parts of the world, such those stored in existing databases (e.g., NIH catalog provided at (https://research.nhgri.nih.gov/atlas/).

Thus, in example embodiments, using a 3D camera (e.g., a true depth camera) on the mobile device 152 such as but not limited to a smartphone or tablet, the mobile device user can take a picture of an individual suspected of having a teratogenic or genetic syndrome and upload it to the remote processor 154 where it can be analyzed, used for machine learning to automatically recognize one or more anomalies relating to specific syndromes, and/or be viewed by an expert, such as a dysmorphologist or clinical geneticist, in a remote location via a VR environment provided by the VR device 156 for a manual assessment. In example methods, the generated 3D image can further be manipulated in three dimensions and measurements can be computed all in the virtual reality context, using a portable VR device.

While such example methods and systems are described herein in the diagnosis of fetal alcohol syndrome particularly, example methods and systems (including the mobile device 152, mobile application, remote processor 154, machine learning algorithm, VR device 156, and/or VR device application) are not intended to be limited to FAS conditions but could be used to identify numerous genetic or teratogenic insults.

A person of ordinary skill in the art would understand that the example applications may be implemented in the mobile communication device (and/or VR device, which also provides a mobile communication device) 20, 152, 156 by one or more modules described herein as well any other additional modules such that a person of ordinary skill in the art may refer to such embodiments as an application platform. Further, the modules and functions thereof may be combined or separated. In addition, such modules can be separated and portions thereof may be implemented across many devices or combined into one device.

Persons of ordinary skill in the art will understand that embodiments of example methods may include a subset of the steps shown and described in the figures as well as the order of the steps may be rearranged. Further, additional steps may be implemented by the method before, after, and in between the steps shown and described in the figures. In addition, the steps of example methods may be implemented by one or more modules executed by one or more computing devices as described herein.

In addition, the mobile communication device(s) 20, 152, 156 preferably also has/have one or more communication interfaces. Each of the communication interfaces may be software or hardware associated in communicating to other devices. The communication interfaces may be of different types that include a user interface, USB, Ethernet, Wi-Fi, wireless, optical, cellular, or any other communication interface coupled to a communication network.

The mobile communication device(s) 20, 152, 156 may include one or more processors that may be co-located with each other or may be located in one module or in different parts of a computing device, or among a plurality of computing devices. The memory may include one or more storage devices that may be co-located with each other or may be located in one module, in different parts of a computing device or among a plurality of computing devices. Types of memory may include, but are not limited to, electronic memory, optical memory, and removable storage media. An intra-device communication link between processor(s), memory device(s), modules, antennas, and communication interfaces may be one of several types that include a bus or other communication mechanism.

The modules disclosed herein may be implemented by the one or more processors. Further, the modules and functions thereof may be combined or separated. In addition, such modules can be separated and portions thereof may be implemented across many devices or combined into one device.

Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. Also, in the foregoing description, numerous details are set forth to further describe and explain one or more embodiments. These details include system configurations, block module diagrams, flowcharts (including transaction diagrams), and accompanying written description. While these details are helpful to explain one or more embodiments of the disclosure, those skilled in the art will understand that these specific details are not required in order to practice the embodiments.

As will be appreciated by one skilled in the art, aspects of the present disclosure may be embodied as an apparatus that incorporates some software components. Accordingly, some embodiments of the present disclosure, or portions thereof, may combine one or more hardware components such as microprocessors, microcontrollers, or digital sequential logic, etc., such as a processor, or processors, with one or more software components (e.g., program code, firmware, resident software, micro-code, etc.) stored in a tangible computer-readable memory device such as a tangible computer memory device, that in combination form a specifically configured apparatus that performs the functions as described herein. These combinations that form specially-programmed devices may be generally referred to herein as modules. The software component portions of the modules may be written in any computer language and may be a portion of a monolithic code base, or may be developed in more discrete code portions such as is typical in object-oriented computer languages. In addition, the modules may be distributed across a plurality of computer platforms, servers, terminals, mobile devices and the like. A given module may even be implemented such that the described functions are performed by separate processors and/or computing hardware platforms.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

Those of ordinary skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of ordinary skill in the art would further appreciate that the various illustrative logical blocks, modules, circuits, and process steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in various ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or process described in connection with the embodiments discloses herein may be embodied directly in hardware, in a software module executed by a processor, or in a combination of the two. A software module may reside in RAM memory, flash memory, ROM memory, EPROM memory, EEPROM memory, registers, hard disk, solid state disk, optical media (e.g., CD-ROM), or any other form of transitory or non-transitory storage medium known in the art. An exemplary storage medium can be coupled to the processor such that the processor can read information from, and write information to, the storage medium. In the alternative, the storage medium can be integral to the processor. The processor and the storage medium may reside in an ASIC. The ASIC may reside in a user terminal. In the alternative, the processor and the storage medium may reside as discrete components in a user terminal.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A computer-assisted method for assisting in anomaly identification relating to fetal alcohol spectrum disorders (FASD) comprising:
   retrieving and/or generating a sequence of progressively changing images that depict morphing of at least:
   a subject's upper lip (vermillion) between at least a first state representing an identification of a first facial anomaly relating to fetal alcohol syndrome (FAS) and a second state representing lack of the identification of the first facial anomaly; and/or
   ridges running from the subject's nose to the subject's lip (philtrum) between at least a first state representing an identification of a second facial anomaly relating to fetal alcohol syndrome (FAS) and a second state representing a lack of the identification of the second facial anomaly;
   wherein the number of images in the sequence is selected to provide a substantially continuous transition between the first and second states;
   displaying the retrieved and/or generated images as the sequence on a display of a processing device;
   providing a user interface on the processing device for a user to navigate the displayed sequence and make an image selection;
   determining a representative image selection based on the user's image selection; and
   providing a determined identification or lack of identification of the first and/or second facial anomaly based on the determined representative image selection.

2. The method of claim 1, wherein said providing comprises:
   processing, by the processing device, the representative image selection to determine an identification or lack of identification of the first and/or second facial anomaly; and
   displaying the determined identification or lack of identification of the first and/or second facial anomaly on the processing device.

3. The method of claim 2, wherein said processing comprises:
comparing the representative image selection to previously-stored data associating the representative image selection with an identification or lack of identification of the first and/or second facial anomaly; and
determining the identification or lack of identification of the first and/or second facial anomaly based on said comparing.

4. The method of claim 1, wherein said providing comprises:
transmitting the representative image selection to an additional processing device for determining an identification or lack of identification of the first and/or second facial anomaly;
receiving the determined identification or lack of identification of the first and/or second facial anomaly from the additional processing device; and
displaying the determined identification or lack of identification of the first and/or second facial anomaly on the processing device.

5. The method of claim 1, wherein said generating a sequence of progressively changing images comprises:
providing at least one base image;
altering the at least one base image to provide, between the altered image and the at least one base image, at least a beginning image and a final image; and
generating remaining images in the sequence by progressively altering the at least one base image, beginning image, and/or final image.

6. A system for assisting in anomaly identification relating to fetal alcohol spectrum disorders (FASD), the system comprising:
a first processing device comprising:
a processor;
a memory; and
executed instructions stored on a non-transitory medium that when executed by the processor cause the processor to perform the method of claim 1.

7. A system for assisting in anomaly identification relating to fetal alcohol spectrum disorders (FASD), the system comprising:
a first processing device comprising:
a first processor;
a first memory; and
executed instructions stored on a non-transitory medium that when executed by the first processor cause the first processor to:
retrieve and/or generating a sequence of progressively changing images that depict morphing of at least:
a subject's upper lip (vermillion) between at least a first state representing an identification of a first facial anomaly relating to fetal alcohol syndrome (FAS) and a second state representing lack of the identification of the first facial anomaly; and/or
ridges running from the subject's nose to the subject's lip (philtrum) between at least a first state representing an identification of a second facial anomaly relating to fetal alcohol syndrome (FAS) and a second state representing a lack of the identification of the second facial anomaly;
wherein the number of images in the sequence is selected to provide a substantially continuous transition between the first and second states;
display the retrieved and/or generated images as the sequence on a display of the first processing device;
provide a user interface on the first processing device for a user to navigate the displayed sequence and make an image selection; and
determine a representative image selection based on the user's image selection; and
a second processing device in communication with said first processing device comprising:
a second processor;
a second memory; and
executed instructions stored on a non-transitory medium that when executed by the second processor cause the second processor to:
determine an identification or lack of identification of the first and/or second facial anomaly based on the determined representative image selection from the first processing device.

8. A computer-assisted method for assisting in anomaly identification relating to a dysmorphology analysis comprising:
retrieving and/or generating a sequence of progressively changing images that depict morphing of at least:
a subject's first physical feature, between at least a first state representing an identification of a first anomaly relating to a dysmorphology and a second state representing lack of the identification of the first anomaly; and/or a subject's second physical feature, between at least a first state representing an identification of a second anomaly relating to the dysmorphology and a second state representing a lack of the identification of the second anomaly;
wherein the number of images in the sequence is selected to provide a substantially continuous transition between the first and second states;
displaying the retrieved and/or generated images as the sequence on a display of a processing device;
providing a user interface on the processing device for a user to navigate the displayed sequence and make an image selection;
determine a representative image selection based on the user's image selection;
processing the representative image selection to determine an identification or lack of identification of the first and/or second anomaly; and
displaying the determined identification or lack of identification of the first and/or second anomaly.

9. The method of claim 8, wherein the method further comprises:
transmitting the representative image selection from a first processing device to a second processing device; and
receiving, by the first processing device, the determined identification or lack of identification of the first and/or second anomaly from the second processing device;
wherein the first processing device performs at least said receiving and/or generating, said displaying the retrieved and/or generated images, and said providing a user interface; and
wherein the second processing device performs at least said processing the representative image selection.

10. The method of claim 8, wherein said generating a sequence of progressively changing images comprises:
providing at least one base image;
altering the at least one base image to provide, between the altered image and the at least one base image, at least a beginning image and a final image; and
generating remaining images in the sequence by progressively altering the at least one base image, beginning image, and/or final image.

11. The method of claim 8, wherein said processing the representative image selection comprises:
comparing the representative image selection to previously-stored data associating the representative image selection with an identification or lack of identification of the first and/or second anomaly of the presence or absence of FAS; and
determining the identification or lack of identification of the first and/or second anomaly based on said comparing.

12. A computer-assisted method for assisting in anomaly identification relating to a dysmorphology analysis comprising the method of claim 1 and comprising:
retrieving and/or generating a sequence of progressively changing images that depict morphing of at least:
a subject's first physical feature, between at least a first state representing an identification of a first anomaly relating to a dysmorphology and a second state representing lack of the identification of the first anomaly; and/or a subject's second physical feature, between at least a first state representing an identification of a second anomaly relating to the dysmorphology and a second state representing a lack of the identification of the second anomaly;
wherein the number of images in the sequence is selected to provide a substantially continuous transition between the first and second states;
displaying the retrieved and/or generated images as the sequence on a display of a processing device;
providing a user interface on the processing device for a user to navigate the displayed sequence and make an image selection;
determining a representative image selection based on the user's image selection;
transmitting the representative image selection to the additional processing device; and
receiving a determined identification or lack of identification of the first and/or second anomaly from the additional processing device based on the transmitted representative image; and
displaying the determined identification or lack of identification of the first and/or second anomaly.

13. A system for assisting in anomaly identification relating to a dysmorphology analysis, the system comprising:
a first processing device comprising:
a processor;
a memory; and
executed instructions stored on a non-transitory medium that when executed by the processor cause the processor to perform the method of claim 12.

14. A method for assisting in identification of an anomaly relating to a dysmorphology analysis in an individual, the method comprising the method of claim 1 and comprising:
acquiring, by a mobile device, a three-dimensional model (3D model) of a face of the individual using a three-dimensional camera controlled by the mobile device;
transmitting, by the mobile device, the acquired three-dimensional model to a remote processor via a communication channel for performing a machine learning algorithm on the acquired 3D model to generate a prediction of the anomaly;
receiving, by the mobile device observational data from at least one VR device, the VR device being configured to receive the generated prediction of the anomaly from the remote processor and display the generated prediction and the 3D model.

15. The method of claim 14, further comprising:
measuring, by the mobile device, one or more facial features in the acquired 3D model; and
transmitting, by the mobile device, the measured one or more facial features via the communication channel.

16. The method of claim 14, further comprising:
performing, by the remote processor, the machine learning algorithm on the acquired 3D model to generate the prediction of the anomaly;
wherein said performing comprises:
receiving the acquired 3D model from the mobile device;
generating a heat map using the acquired 3D model;
comparing the generated heat map to one or more signature heat maps corresponding to the anomaly; and
generating the prediction based on said comparison.

17. The method of claim 16, further comprising:
training the machine learning algorithm using a set of stored heat maps and corresponding identified anomalies.

18. The method of claim 16, further comprising:
combining, by the remote processor, the generated prediction and the received 3D model; and
transmitting, by the remote processor, the combined prediction and 3D model to the VR device via a second communication channel.

19. The method of claim 14, further comprising:
receiving, by the VR device, the generated prediction of the anomaly and the acquired 3D model from the remote processor via a second communication channel;
displaying the generated prediction and the 3D model as a 3D VR display on the VR device;
receiving observational data by a user of the 3D VR display via a user interface of the VR device; and
transmitting, by the VR device, the received observational data to the mobile device.

20. A system for assisting in identification of an anomaly relating to a dysmorphology analysis in an individual, the system comprising the method of claim 1 and comprising:
a mobile device configured to acquire a three-dimensional model (3D model) of a face of the individual using a three-dimensional camera controlled by the mobile device;
a remote processor configured to receive the acquired three-dimensional model from the mobile device via a first communication channel and perform a machine learning algorithm on the acquired 3D model to generate a prediction of the anomaly;
at least one VR device configured to receive the generated prediction of the anomaly from the remote processor via a second communication channel and display the generated prediction and the 3D model, and to receive observational data from a user of the VR device; and
an electronic medical records (EMR) database in communication with the remote processor for exchanging information with the remote processor.

* * * * *